(12) United States Patent
Biset et al.

(10) Patent No.: US 9,839,729 B2
(45) Date of Patent: *Dec. 12, 2017

(54) BLOOD BAG SYSTEM AND CASSETTE

(71) Applicant: TERUMO KABUSHIKI KAISHA, Shibuya-ku, Tokyo (JP)

(72) Inventors: Roland Biset, Leuven (BE); Makoto Hirabuki, Leuven (BE)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 207 days.

This patent is subject to a terminal disclaimer.

(21) Appl. No.: 14/679,636

(22) Filed: Apr. 6, 2015

(65) Prior Publication Data

US 2015/0209495 A1 Jul. 30, 2015

Related U.S. Application Data

(63) Continuation of application No. 13/131,054, filed as application No. PCT/JP2009/069894 on Nov. 18, 2009, now abandoned.

(30) Foreign Application Priority Data

Nov. 28, 2008 (JP) .................................. 2008-305211

(51) Int. Cl.
  *A61B 19/00* (2006.01)
  *A61M 1/02* (2006.01)
  (Continued)

(52) U.S. Cl.
  CPC .............. *A61M 1/0218* (2014.02); *A61J 1/10* (2013.01); *A61M 1/029* (2013.01);
  (Continued)

(58) Field of Classification Search
  CPC .. A61M 1/0218; A61M 1/0227; A61M 1/029; A61M 1/3693; B01D 21/262;
  (Continued)

(56) References Cited

U.S. PATENT DOCUMENTS

| 4,322,298 A | 3/1982 | Persidsky |
| 5,092,996 A | 3/1992 | Spielberg |

(Continued)

FOREIGN PATENT DOCUMENTS

| CA | 2688262 A1 | 12/2008 |
| CN | 1634615 A | 7/2005 |

(Continued)

OTHER PUBLICATIONS

International Search Report (PCT/ISA/210) dated May 7, 2010, by European Patent Office as the International Searching Authority for International Application No. PCT/JP2009/069894.

(Continued)

*Primary Examiner* — Tatyana Zalukaeva
*Assistant Examiner* — Ariana Zimbouski
(74) *Attorney, Agent, or Firm* — Buchanan Ingersoll & Rooney PC

(57) ABSTRACT

A blood bag system includes a BC pooling bag for centrifugation of a buffy coat, a filter for removing white blood cells from a supernatant liquid transferred from the BC pooling bag, a platelet preserving bag for reserving the supernatant liquid that has passed through the filter, a first tube connecting the BC pooling bag and an inlet of the filter, a second tube connecting the platelet preserving bag and an outlet of the filter, and a cassette to be fixed in the centrifugation and separation apparatus. The first tube and the second tube are disposed within the cassette. The cassette includes a first (Continued)

clamp section for closing and opening the first tube, and a second clamp section for closing and opening the second tube.

24 Claims, 19 Drawing Sheets

(51) Int. Cl.
    *A61M 1/36*     (2006.01)
    *B04B 5/04*     (2006.01)
    *A61J 1/10*     (2006.01)
    *B01D 21/26*     (2006.01)
    *B04B 7/16*     (2006.01)

(52) U.S. Cl.
    CPC ........ *A61M 1/0227* (2014.02); *A61M 1/3693* (2013.01); *B01D 21/262* (2013.01); *B04B 5/0428* (2013.01); *B04B 7/16* (2013.01); *A61M 2205/12* (2013.01); *B04B 2005/0435* (2013.01); *B04B 2005/0478* (2013.01)

(58) Field of Classification Search
    CPC ....... B04B 5/0428; B04B 5/0442; B04B 7/16; B04B 2005/0435; A61J 1/10
    See application file for complete search history.

(56) References Cited

U.S. PATENT DOCUMENTS

| | | | |
|---|---|---|---|
| 5,670,060 | A | 9/1997 | Matkovich et al. |
| 6,049,727 | A | 4/2000 | Crothall |
| 6,348,156 | B1 * | 2/2002 | Vishnoi ............... A61M 1/3496 210/103 |
| 6,605,223 | B2 | 8/2003 | Jorgensen et al. |
| 6,742,760 | B2 | 6/2004 | Blickhan et al. |
| 7,234,677 | B2 | 6/2007 | Zerfas |
| 7,264,608 | B2 | 9/2007 | Bischof et al. |
| 2003/0034312 | A1 | 2/2003 | Unger et al. |
| 2003/0176267 | A1 | 9/2003 | Eberle |
| 2004/0026341 | A1 | 2/2004 | Hogberg et al. |
| 2004/0104182 | A1 | 6/2004 | Holmes et al. |
| 2004/0238444 | A1 * | 12/2004 | Ragusa ............... A61M 1/0209 210/645 |
| 2005/0020978 | A1 * | 1/2005 | Vollenweider ...... A61M 39/281 604/151 |
| 2005/0049539 | A1 | 3/2005 | O'Hara, Jr. et al. |
| 2005/0274673 | A1 * | 12/2005 | Corbin, III .......... A61M 1/0209 210/645 |
| 2006/0205581 | A1 * | 9/2006 | Chammas ........... A61M 1/3693 494/16 |
| 2006/0287628 | A1 | 12/2006 | Hirabuki |
| 2008/0053203 | A1 | 3/2008 | Hogberg et al. |
| 2008/0096749 | A1 | 4/2008 | Hlavinka et al. |
| 2009/0049662 | A1 | 2/2009 | Miller |
| 2009/0286221 | A1 | 11/2009 | Klip et al. |

FOREIGN PATENT DOCUMENTS

| | | |
|---|---|---|
| EP | 1216099 B1 | 5/2008 |
| JP | 7-507717 A | 8/1995 |
| WO | WO 93/25295 A1 | 12/1993 |
| WO | WO 02/053289 A2 | 7/2002 |
| WO | WO 2008/002135 A1 | 1/2008 |

OTHER PUBLICATIONS

Written Opinion (PCT/ISA/237) dated May 7, 2010, by European Patent Office as the International Searching Authority for International Application No. PCT/JP2009/069894.

Official Action issued by Chinese Patent Office dated Jun. 20, 2013 in Chinese Application No. 200980145435.2, and English language translation of Official Action (11 pgs).

Official Action issued by Russian Patent Office dated Apr. 17, 2013 in Russian Application No. 2011126336, and English language translation of Official Action (7 pgs).

Official Action dated Aug. 31, 2017 issued by the Indian Patent Office in corresponding Indian Patent Application No. 3980/DELNP/2011 (5 pages).

* cited by examiner

BLOOD BAG SYSTEM AND CASSETTE

CROSS-REFERENCES TO RELATED APPLICATIONS

This application is a continuation of U.S. application Ser. No. 13/131,054 filed on May 25, 2011, which is a U.S. national stage application based on International Application No. PCT/JP2009/069894 having an international filing date of Nov. 18, 2009 and which claims priority to Japanese Application No. 2008-305211 filed on Nov. 28, 2008, the entire content of each of which is incorporated herein by reference.

TECHNICAL FIELD

The present invention relates to a blood bag system and a cassette to be mounted in a centrifugation and separation apparatus or the like, for centrifuging whole blood or a blood component (buffy coat or the like) prepared from whole blood into a supernatant liquid and a sedimentary liquid and transferring the supernatant liquid.

BACKGROUND ART

Hitherto, whole blood transfusion in which all the components of blood obtained by blood donation are subjected to transfusion has been the mainstream of blood transfusion. Attendant on the recent progress of technologies, however, blood component transfusion has come to be conducted in which the obtained blood is divided into blood components, such as red blood cells, platelets and plasma, and only the blood component needed by a patient is subjected to transfusion. With blood component transfusion, it is possible to alleviate the burden on the patient's circulatory system and other side effects, and effective utilization of the donated blood is promised.

When subjected to centrifugation, the donated blood is divided into a light supernatant PRP fraction, a heavy sedimentary CRC fraction, and a buffy coat (BC) formed therebetween. The buffy coat contains white blood cells, platelets and red blood cells, and in particular, the platelets include young active platelets in high proportion.

On the other hand, the buffy coat contains white blood cells and therefore cannot be utilized as is. In view of this, it is a common practice to extract only the buffy coat from the centrifuged blood, to subject it again to centrifugation so as to separate the buffy coat into a supernatant liquid and a sedimentary liquid, and further to remove white blood cells from a supernatant liquid by a white blood cell removing filter (see, for example, Patent Document 1).

Patent Document 1
Japanese Laid-Open Patent Publication No. 07-507717 (PCT) (WO93/25295A1)

SUMMARY

In order to centrifuge a buffy coat into a supernatant liquid and a sedimentary liquid and to transfer the supernatant liquid as mentioned above, it is necessary to perform centrifugation in a former step and to separate (transfer) in a latter step. Accordingly, two special purpose apparatuses are needed therefor, with troublesome operations.

It is preferable that a centrifugation and separation apparatus, which is capable of simultaneously carrying out the two steps, is put to practical use. As such a centrifugation and separation apparatus, a centrifugation means and a separation means (transfer means) may be provided, so that a desired treatment will be carried out by use of a predetermined disposable blood bag system. As for such a blood bag system to be used in the centrifugation and separation apparatus, in general, the following configuration may be considered. The system includes a first bag in which the buffy coat is reserved and in which the buffy coat is centrifuged into a supernatant liquid and a sedimentary liquid, a filter for removing white blood cells from the supernatant liquid transferred by pressing the first bag by a predetermined pressing means, a second bag for reserving the supernatant liquid deprived of the white blood cells by the filter, a first tube for connecting the first bag and an inlet of the filter, a second tube for connecting the second bag and an outlet of the filter, and a first clamp and a second clamp for closing and opening the first tube and the second tube.

In order to mount such a blood bag system in a centrifugation and separation apparatus, however, the first bag, the second bag and the filter must be disposed in appropriate positions, and the first tube, the second tube, the first clamp and the second clamp must be disposed along appropriate paths. This leads to a complicated procedure as well as a fear of mismounting.

The present invention has been made in consideration of the above-mentioned problems. Accordingly, it is an object of the invention to provide a blood bag system and a cassette therefor to be mounted in a centrifugation and separation apparatus for centrifuging a buffy coat obtained from whole blood into a supernatant liquid and a sedimentary liquid and transferring the supernatant liquid, wherein the blood bag system and the cassette can be mounted in the centrifugation and separation apparatus readily and accurately.

According to the present invention, there is provided a blood bag system including a first bag for reserving whole blood or a blood component, a filter having a filter medium for removing predetermined cells from a blood component obtained by centrifugation of the liquid contained in the first bag, a second bag for reserving a blood component obtained upon removal of the predetermined cells by the filter, a first tube for connecting the first bag and an inlet of the filter, a second tube for connecting the second bag and an outlet of the filter, and a cassette for holding a part of the first tube and a part of the second tube, wherein the cassette has a first clamp section for closing and opening the first tube, and a second clamp section for closing and opening the second tube.

According to the present invention, there also is provided a cassette mounted to a multiple bag including a first bag for reserving whole blood or a blood component, a filter having a filter medium for removing predetermined cells from a blood component obtained by centrifugation of the liquid contained in the first bag, a second bag for reserving a blood component obtained upon removal of the predetermined cells by the filter, a first tube for connecting the first bag and an inlet of the filter, and a second tube for connecting the second bag and an outlet of the filter, wherein the cassette holds a part of the first tube and a part of the second tube, and includes a first clamp section for closing and opening the first tube, and a second clamp section for closing and opening the second tube.

Thus, the first tube and the second tube are preliminarily arranged properly in the cassette of the blood bag system, and it is sufficient simply to mount the cassette in a predetermined portion of the centrifugation and separation apparatus. Therefore, the need for intricate laying and arrangement of the first and second tubes, and the need for arranging the first and second clamps are eliminated, whereby mounting of the cassette can be carried out easily and assuredly. In addition, the cassette is equipped with the first clamp and the second clamp, and the clamps are arranged properly in relation to the clamp driving means within the centrifugation and separation apparatus.

The first clamp section and the second clamp section may be configured integrally with the cassette. This makes it possible to simply configure the first clamp section and the second clamp section, and to reduce the number of component parts through integral molding. Naturally, therefore, the operator does not need to mount the first clamp and the second clamp to the cassette, so that the cassette can be mounted easily, thereby reducing the possibility of mis-mounting.

A configuration may be adopted wherein the first clamp section and the second clamp section each includes a pressing section which can be elastically advanced and retracted, and which presses the first tube or the second tube from a lateral side thereof, an acute-angular engaged portion provided at a tip of the pressing section, a latch section which can be elastically tilted, and an engaging portion which is provided on the latch section and which engages with the engaged portion of the pressing section while in a state of pressing the first tube or the second tube. This enables the first clamp and the second clamp to be simple in configuration.

According to the present invention, there is further provided a blood bag system including a first bag for reserving whole blood or a blood component, a filter having a filter medium for removing predetermined cells from a blood component obtained by centrifugation of the liquid contained in the first bag, a second bag for reserving a blood component obtained upon removal of the predetermined cells by the filter, a first tube for connecting the first bag and an inlet of the filter, a second tube for connecting the second bag and an outlet of the filter, a first clamp for closing and opening the first tube, a second clamp for closing and opening the second tube, and a cassette for holding a part of the first tube, a part of the second tube, the first clamp and the second clamp, wherein the cassette has a first clamp operating section for operating the first clamp, and a second clamp operating section for operating the second clamp.

According to the present invention, there is also provided a cassette mounted to a multiple bag including a first bag for reserving whole blood or a blood component, a filter having a filter medium for removing predetermined cells from a blood component obtained by centrifugation of the liquid contained in the first bag, a second bag for reserving a blood component obtained upon removal of the predetermined cells by the filter, a first tube for connecting the first bag and an inlet of the filter, a second tube for connecting the second bag and an outlet of the filter, a first clamp for closing and opening the first tube, and a second clamp for closing and opening the second tube, wherein the cassette holds a part of the first tube and a part of the second tube, and includes a first clamp operating section for operating the first clamp, and a second clamp operating section for operating the second clamp.

Thus, the first tube and the second tube are preliminarily arranged properly within the cassette of the blood bag system, and it is sufficient for the cassette to be mounted in a predetermined portion of a centrifugation and separation apparatus. Therefore, the need for intricate laying and arrangement of the first and second tubes, and the need for arranging the first and second clamps are eliminated, whereby mounting of the cassette can be carried out easily and assuredly. In addition, the first clamp and the second clamp are held by the cassette, and therefore the clamps are properly arranged in relation to the clamp driving means within the centrifugation and separation apparatus.

In addition, general-purpose clamp or the like can be utilized as the first clamp and the second clamp. Since the first clamp and the second clamp are preliminarily held properly by the cassette, it is unnecessary for the operator to mount the first clamp and the second clamp onto the cassette. Therefore, the required procedure is easy to carry out, and moreover, there is no possibility of misarrangement.

The first clamp operating section and the second clamp operating section may be configured integrally with the cassette.

The first clamp operating section and the second clamp operating section may each includes a pressing section which can be elastically advanced and retracted, and which presses the first tube or the second tube from a lateral side thereof through the first clamp and the second clamp, an acute-angular engaged portion provided at a tip of the pressing section, a latch section which can be elastically tilted, and an engaging portion, which is provided on the latch section, and which engages with the engaged portion of the pressing section while in a state of pressing the first tube or the second tube through the first clamp and the second clamp. This enables the first clamp operating section and the second clamp operating section to be simple in configuration.

When the first clamp and the second clamp are arranged in parallel with each other within the cassette, a parallel arrangement surface can be utilized effectively, and good balance is secured.

It is preferable that whole blood or a blood component collected from a plurality of donors is reserved in the first bag, and the blood bag system is mounted in a centrifugation and separation apparatus for centrifuging the liquid contained in the first bag into a supernatant liquid and a sedimentary liquid, thereby removing a predetermined component from the supernatant liquid by the filter, and for transferring (separating) the supernatant liquid, deprived of the predetermined component, into the second bag.

A configuration may be adopted in which the centrifugation and separation apparatus includes a first sensor and a second sensor, each of which has a light emitting section and a light receiving section, and which detects the kind of liquid passing between the light emitting section and the light receiving section, the cassette has a sensor hole in which the first sensor and the second sensor are inserted, and the first tube is located so as to pass between the light emitting section and the light receiving section of the first sensor, whereas the second tube is located so as to pass between the light emitting section and the light receiving section of the second sensor. This makes it possible to assuredly detect the liquids present in the first tube and the second tube.

According to the blood bag system and the cassette pertaining to the present invention, the first tube and the second tube are preliminarily arranged properly within the cassette of the blood bag system, and it is sufficient for the cassette to be mounted in a predetermined portion of a predetermined centrifugation and separation apparatus or the like. Therefore, the need for intricate laying and arrangement of the first and second tubes, and the need for arranging the first and second clamps are eliminated, whereby the required mounting can be carried out easily and assuredly. In addition, the first clamp section and the second clamp section are provided in or the first clamp and the second clamp are held in the cassette, so that the clamp sections or clamps are properly arranged in relation to clamp driving means within the centrifugation and separation apparatus or the like.

DESCRIPTION OF EMBODIMENTS

A blood bag system and the cassette according to the present invention will be described below, in which embodiments thereof are shown and described with reference to the accompanying FIGS. 1 to 19.

Blood bag systems 10a, 10b, 10c, 10d and cassettes 50a, 50b, 50c, 50d according to first to fourth embodiments are respectively mounted in a centrifugation and separation apparatus 11 for centrifuging whole blood or a blood component (hereinafter, referred to as a buffy coat in the following embodiments) prepared from whole blood into a supernatant liquid and a sedimentary liquid, and for transferring the supernatant liquid. First, the centrifugation and separation apparatus 11 will be described. In the following description, the direction of arrow A in FIG. 2 will be taken as a radial direction, and the direction of arrow B will be taken as a circumferential direction. Strictly speaking, the circumferential direction is the direction along the circular arc, as indicated by arrow B. For convenience of description, however, a direction orthogonal to the arrow A in the location being described will also be referred to as the circumferential direction.

Figure 1:
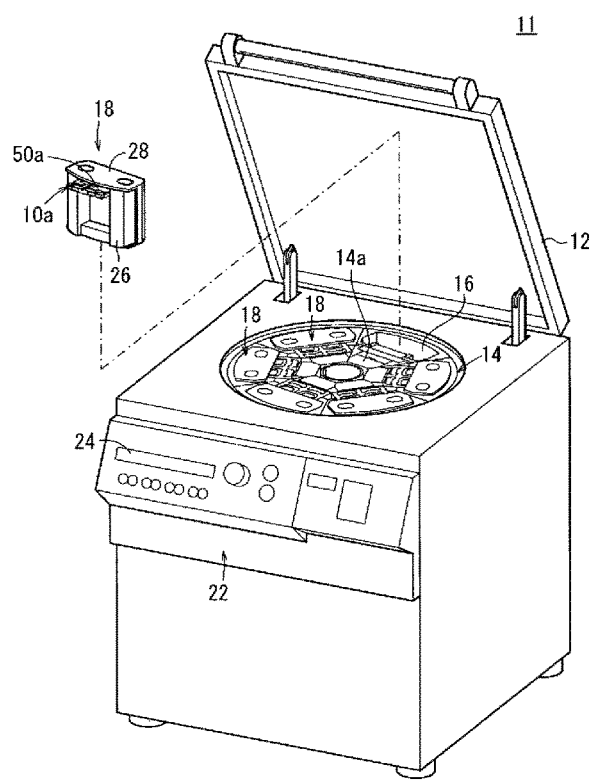
FIG. 1 is a perspective view of a centrifugation and separation apparatus.

As shown in FIG. 1, the centrifugation and separation apparatus 11 has a box-like shape, and includes a top cover 12 which can be opened and closed, a centrifugal drum (centrifugation means) 14 inside the apparatus, six unit insertion holes 16 arranged at regular angular intervals (60°) inside the centrifugal drum 14, six insert units 18 inserted respectively in the unit insertion holes 16, and six pressers (pressing means) 20 (see FIG. 2), which are provided in a central area and which can be advanced and retracted in a rotational radial direction in relation to the insert units 18.

The centrifugation and separation apparatus 11 is operated based on operations performed at a console section 22 provided at the front of the apparatus. Further, the centrifugation and separation apparatus 11 is controlled by a microcomputer (not shown) and can display predetermined information on a monitor 24.

Figure 2:
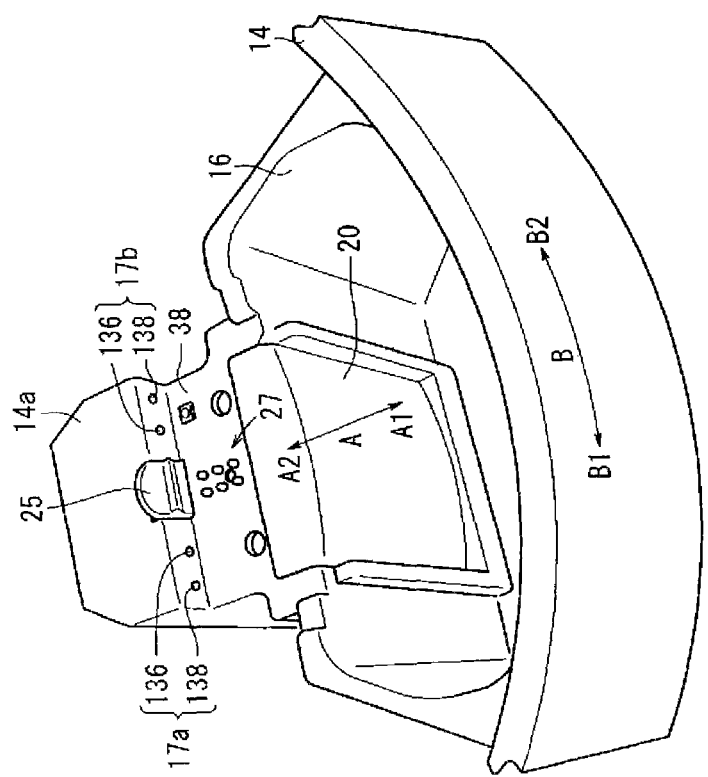
FIG. 2 is a partial enlarged perspective view of a centrifugal drum in the centrifugation and separation apparatus.

As shown in FIG. 2, a central body 14a of the central drum 14 has a holding lever 25, which is urged by an elastic body and which holds an end portion of a cassette holder 38, electrodes 27, first rods 136 and second rods 138, and a presser 20. The first rods 136 and the second rods 138 are provided in two pairs, wherein among these rods, the rods on the first circumferential direction B1 side constitute a first clamp driving means 17a for closing and opening a first clamp section 106 (see FIG. 3), and the rods on the second circumferential direction B2 side constitute a second clamp driving means 17b for closing and opening a second clamp section 108 (see FIG. 3). The section shown in FIG. 2 may be configured as a single unit, and six such units may be combined with each other along the circumferential direction.

Figure 3:
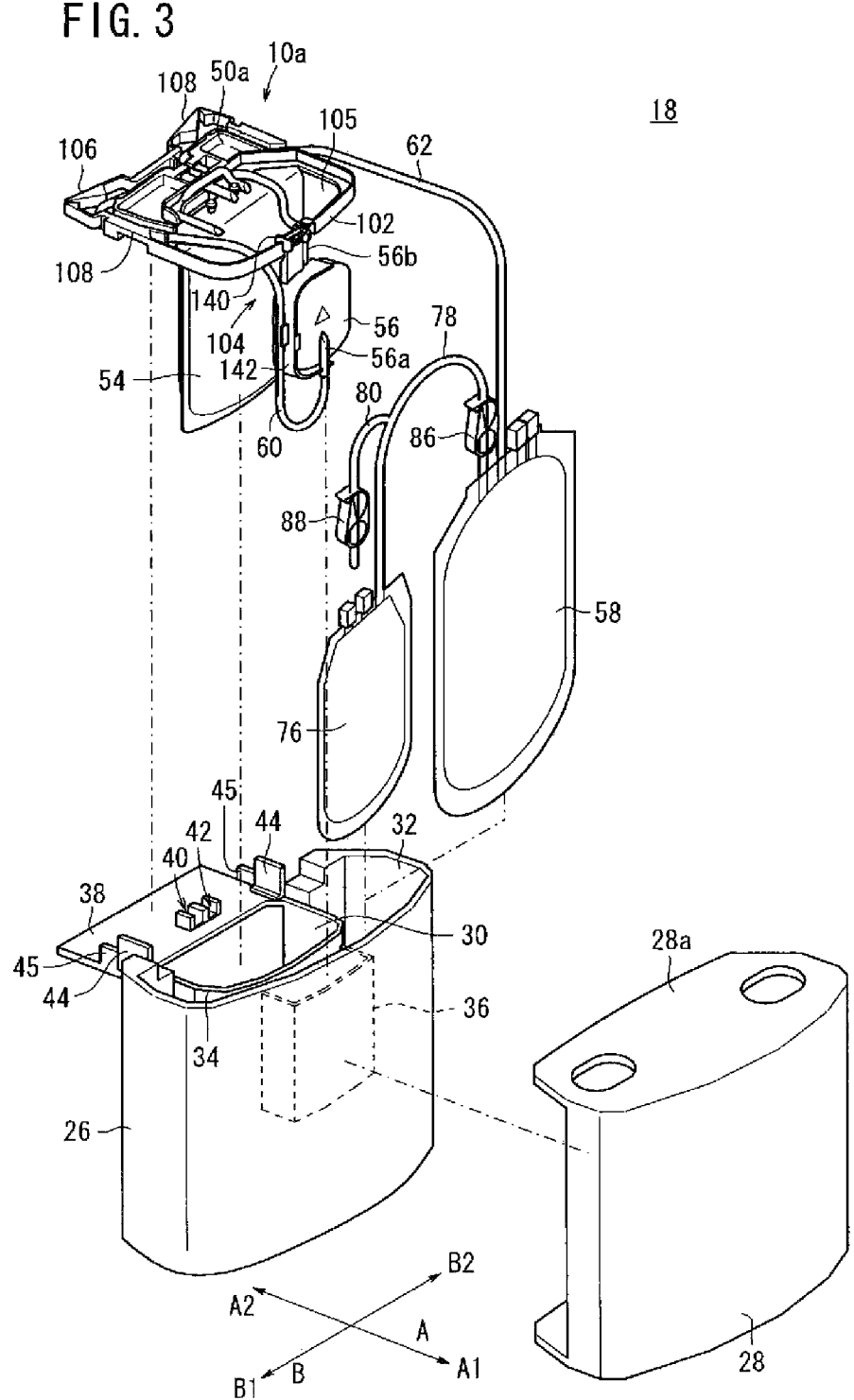
FIG. 3 is an exploded perspective view of an insert unit.

As shown in FIG. 3, the insert unit 18 has a unit body 26, a cover body 28, and the blood bag system 10a. The unit body 26 is a bottomed tube, which has a wide circular arc shape in top plan view and is open at the top, wherein a small chamber (first chamber) 30 on the inner diameter side and a large chamber (second chamber) 32 are partitioned from each other by an arcuate wall 34. A buffy coat pooling bag (first bag) 54 to be described later is disposed within the small chamber 30, while a platelet preserving bag (second bag) 58 and a sampling bag 76 are disposed within the large chamber 32. The platelet preserving bag 58 has a surface area, which is enlarged for securing appropriate oxygen permeability for the platelets reserved therein, and which is set to be larger than the buffy coat pooling bag 54.

The buffy coat pooling bag (BC pooling bag) 54, the platelet reserving bag 58 and the sampling bag 76 are each formed, for example, by a method in which flexible sheet members made of a flexible resin such as polyvinyl chloride and polyolefin are laid on each other, and seal portions at the peripheral edges thereof are joined by fusing (heat fusing, high-frequency fusing) or adhesion in order to obtain a bag-formed body.

The small chamber 30 opens not only at the top but also on the inner diameter side. A filter pocket 36 for holding a filter 56 and an attachment 142, which will be described later, are provided on the outer diameter side of the wall 34. A plate-like cassette holder 38 that projects to the inner diameter side is provided at both end portions on the inner diameter side of the small chamber 30.

The cassette holder 38 includes a first sensor 40 and a second sensor 42 for detecting the kinds of liquids that pass inside a first tube 60 and a second tube 62, both to be described later, as well as detaching levers 44 and holder projections 45 provided on both ends in the circumferential direction. The first sensor 40 and the second sensor 42 include light emitting sections 40a, 42a (see FIG. 9) and light receiving sections 40b, 42b (see FIG. 9), wherein the kind of liquid passing between these sections can be determined based on the degree of transmission of light through the liquid. The light emitting sections 40a, 42a and the light receiving sections 40b, 42b are arranged in parallel with each other, and project slightly upwards at the top surface of the cassette holder 38. A plurality of contacts (not shown) for connection to the first sensor 40 and the second sensor 42, or to interface circuits thereof, are provided at a lower surface of the cassette holder 38. When the contacts are placed in contact with the reception-side electrodes 27 (see FIG. 2) provided on the central body 14a of the centrifugal drum 14, signals from the first sensor 40 and the second sensor 42 can be supplied to the microcomputer.

The cover body 28 includes a cover, which is mounted to the unit body 26 from an outer lateral side thereof. The cover body 28 is capable of covering an outer lateral surface, an upper surface and a lower surface of the unit body 26, and can securely hold the blood bag system 10a mounted on the unit body 26.

Figure 4:
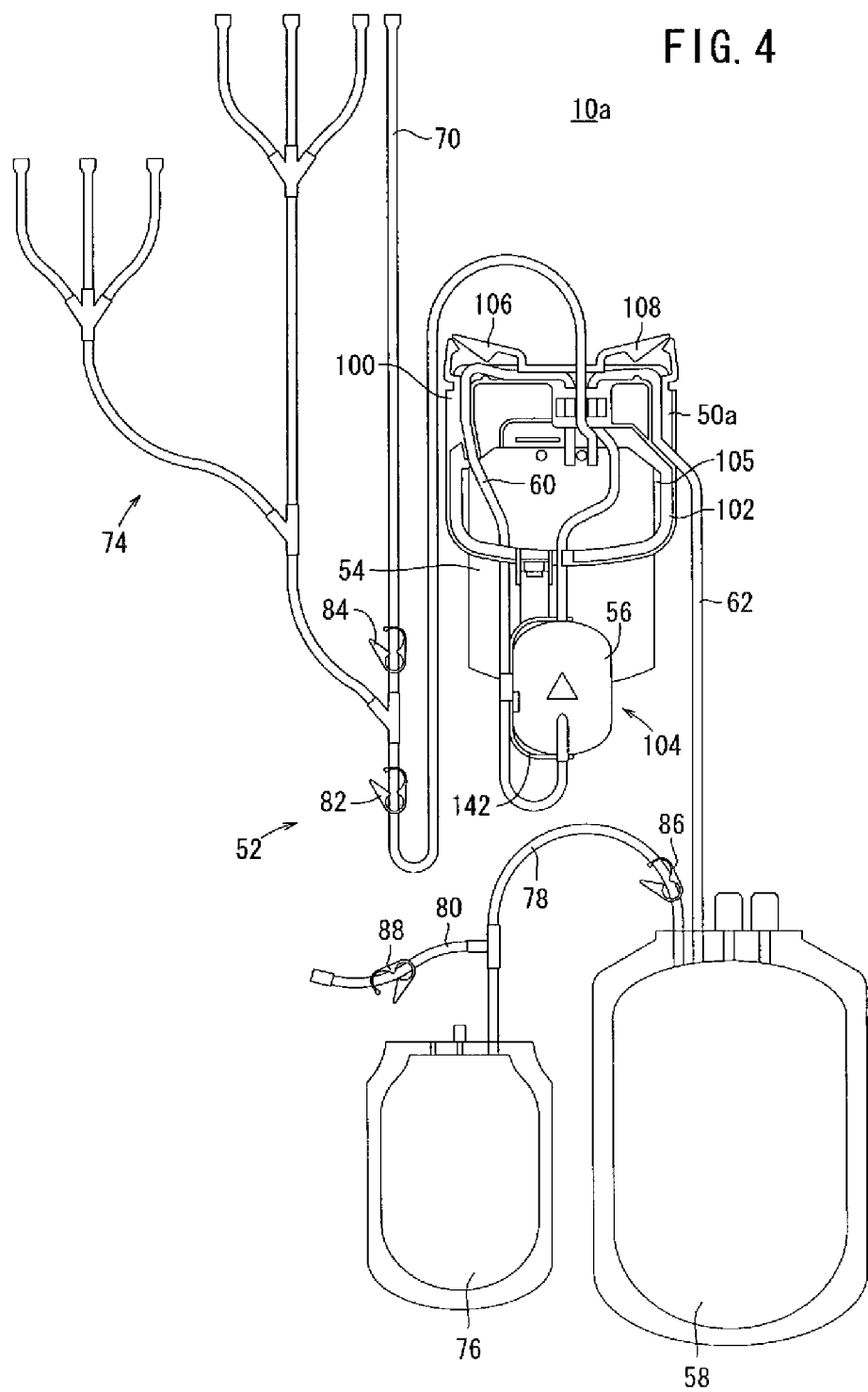
FIG. 4 is a plan view of a blood bag system according to a first embodiment of the present invention.

Next, the blood bag system 10a and the cassette 50a according to the first embodiment will be described below. As shown in FIG. 4, the blood bag system 10a comprises a multiple bag 52 and a cassette 50a.

Figure 5:
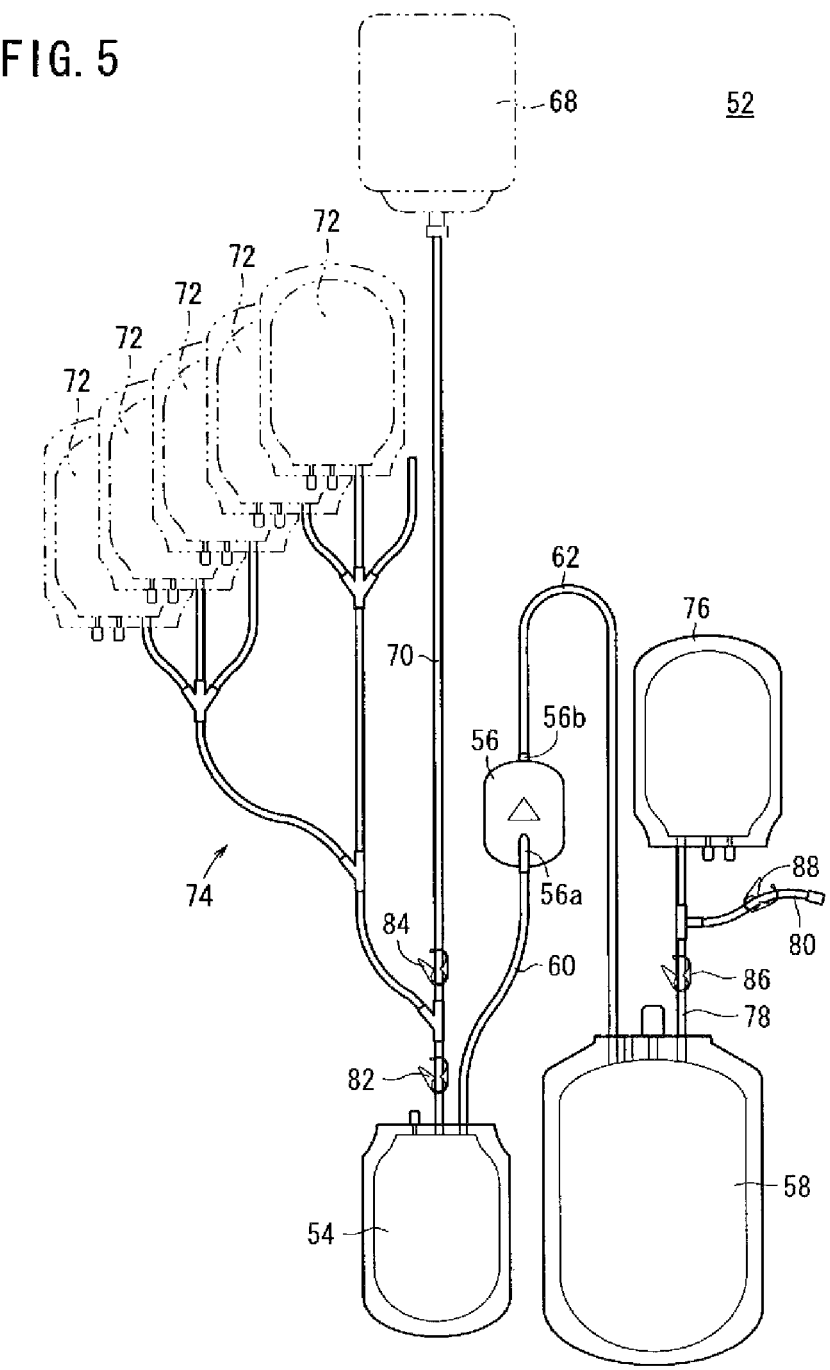
FIG. 5 is a plan view of a multiple bag system.

As shown in FIG. 5, the multiple bag 52 includes the BC pooling bag 54 in which a buffy coat (blood component) is reserved and in which the buffy coat is centrifuged into a supernatant liquid (blood component) and a sedimentary liquid by the centrifugal drum 14, a filter 56 for removing white blood cells (predetermined cells) from the supernatant liquid transferred by pressing the BC pooling bag 54 by the presser 20, the platelet reserving bag 58 for reserving the supernatant liquid obtained upon removal of white blood cells by the filter 56, a first tube 60 for connecting the BC pooling bag 54 and an inlet 56a of the filter 56, and a second tube 62 for connecting the platelet reserving bag 58 and an outlet 56b of the filter 56. The filter 56 preferably is provided with a mark thereon, which is indicative of the blood flow direction.

The filter 56 (see FIG. 13) has a roughly elliptical thin plate-like shape, with the inlet 56a provided on a first surface side at one end thereof, and the outlet 56b provided on a second surface side at the other end thereof. Each of the inlet 56a and the outlet 56b comprises a tubular body, which is elongated in the same direction as the longitudinal direction of the filter 56. Inside the filter 56, a planar filter medium 57 (see FIG. 14) is provided, for partitioning the inside into a first surface side and a second surface side, respectively.

The multiple bag 52 further includes a third tube 70 having an end portion to which a container 68 for a platelet preserving liquid can be connected, and having the other end thereof connected to the BC pooling bag 54, a branched tube 74 which is branched (into six branches, for example, formed through bifurcation and trifurcation) from the third tube 70 and to which a plurality of BC bags 72 can be connected, the sampling bag 76 for sampling the liquid contained in the platelet preserving bag 58, a fourth tube 78 for interconnecting the platelet preserving bag 58 and the sampling bag 76, and a sampling tube 80 that branches from the fourth tube 78. When the blood bag system 10a is mounted in the centrifugation and separation apparatus 11, the third tube 70 is cut after fusing thereof to prevent leakage at a location near the BC pooling bag 54. The portion left upon cutting forms a third tube 70a (see FIG. 7).

The multiple bag 52 includes a clamp 82 provided in the vicinity of an end portion of the third tube 70, a clamp 84 provided on the tip side relative to the branching portion of the third tube 70, a clamp 86 provided in the vicinity of an end portion of the fourth tube 78, and a clamp 88 provided for the sampling tube 80. Each of the tubes in the blood bag system 10a is a transparent flexible resin tube.

The clamp 82, 84, 86, 88 are standard products, which have hitherto been used, and the tubes onto which they are mounted can be closed and opened by operating the clamp 82, 84, 86, 88 with one's fingers. It is recommendable to provide the clamp 82, 84, 86, 88 with different colors according to the position and/or the purpose of use thereof. At times of sterilization and storage of the blood bag system 10a, each of the clamp 82, 84, 86, 88 is in an opened state, so that the inside of the multiple bag 52 is in a mutually connected and uniformly sterilized state.

Each of end portions of the third tube 70, the branched tube 74, and the sampling tube 80 is closed by a predetermined means, and is placed in a sterilized state obtained by being subjected to a predetermined sterilizing treatment (for example, irradiation with γ-rays) together with the cassette 50a.

Incidentally, although for convenience of illustration it is shown in FIG. 5 that the BC bag 72 and the container 68 can be connected to the multiple bag 52 lacking the cassette 50a, in practice the BC bag 72 and the container 68 are connected in a condition where the cassette 50a is provided as the blood bag system 10a (see FIG. 4), as will be described later.

Returning to FIG. 4, the blood bag system 10a includes the multiple bag 52 and the cassette 50a. The cassette 50a is fitted with the first tube 60 and the second tube 62.

Figure 6:
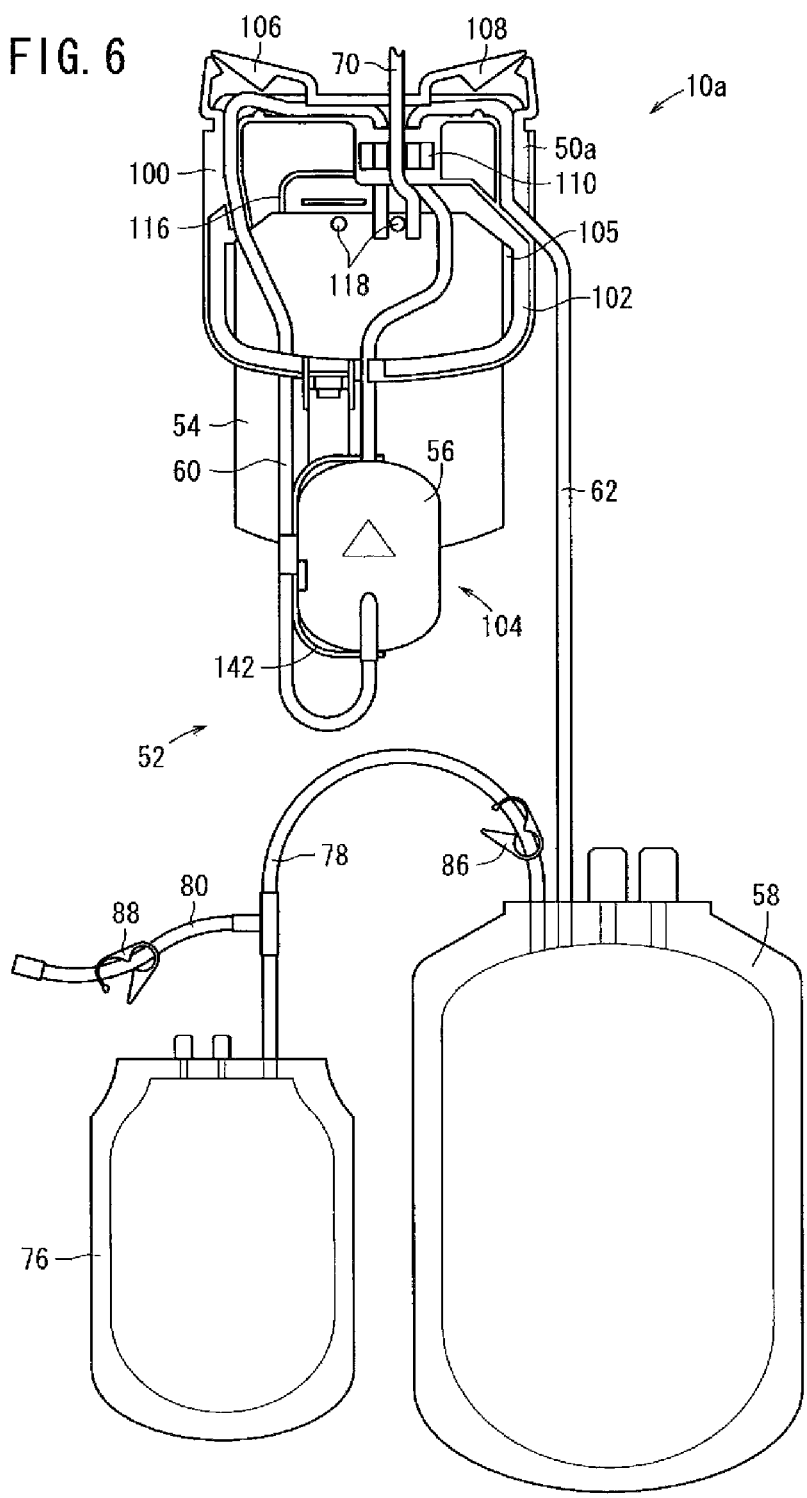
FIG. 6 is a partial enlarged plan view of the blood bag system according to the first embodiment.
Figure 7:
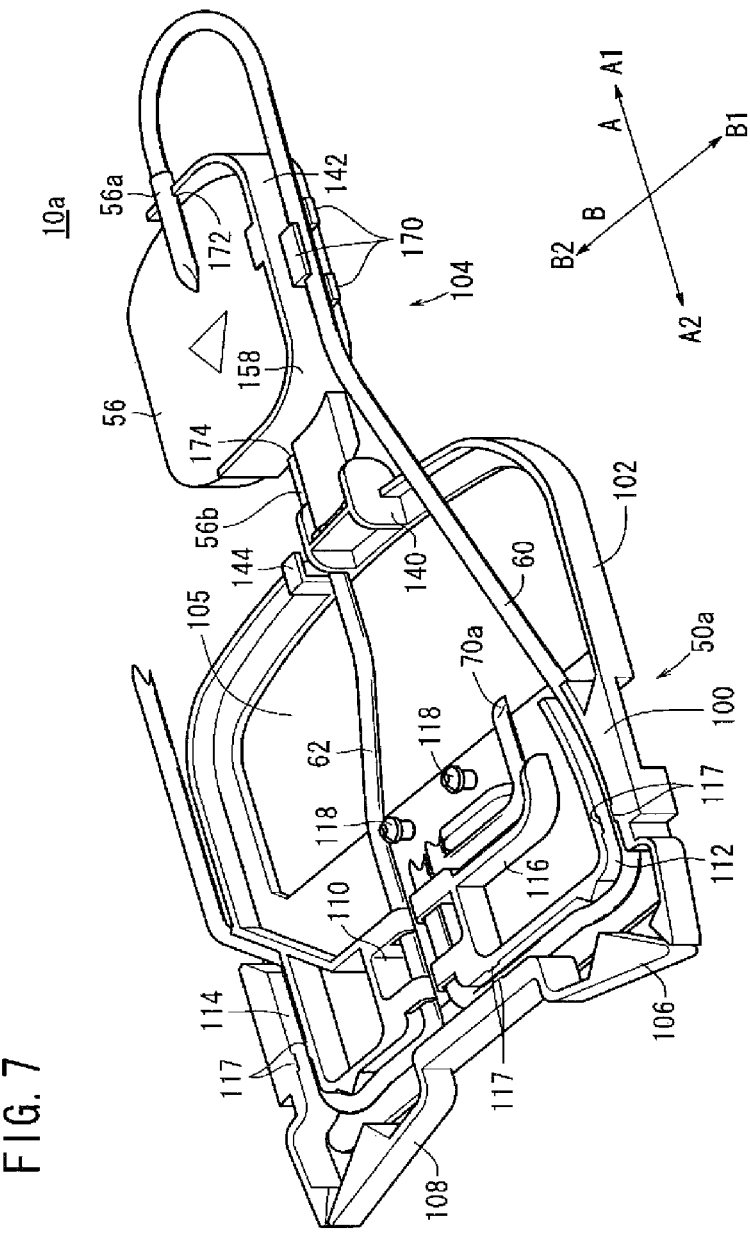
FIG. 7 is a partial enlarged perspective view of the blood bag system according to the first embodiment, in a condition where a filter holder is expanded.
Figure 8:
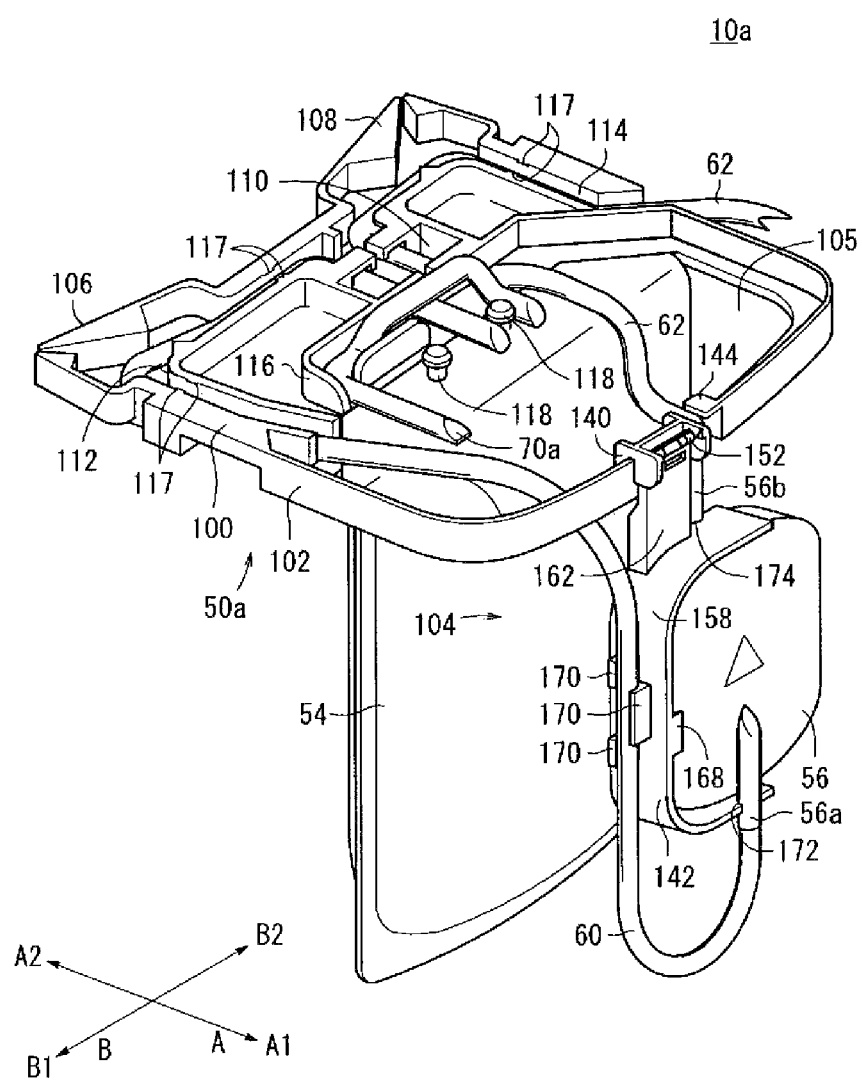
FIG. 8 is a partial enlarged perspective view of the blood bag system according to the first embodiment, in a condition where the filter holder is bent at 90°.

As shown in FIGS. 6, 7 and 8, the cassette 50a includes a plate section 100 to be mounted to the cassette holder 38, an arch section 102 for interconnecting both end portions on the outer side of the plate section 100, and a filter holder 104 connected to a central portion on the outermost diameter side of the arch section 102. The material of the cassette 50a, for example, is PP (polypropylene), POM (polyoxymethylene), or the like.

The arch section 102 is shaped along the top end of the wall 34, and the space surrounded by the outer end surface of the plate section 100 and the arch section 102 has the same shape as the upper surface portion of the small chamber 30, thereby forming a bag hole 105 in which to insert the BC pooling bag 54. A portion of the whole length part of the arch section 102 may be provided with an angled structure so as to enhance strength.

The plate section 100 includes the first clamp section 106 and the second clamp section 108 provided on the inner diameter side by integral molding, a sensor hole 110 which is provided at a roughly central portion and in which the first sensor 40 and the second sensor 42 are inserted, a first guide passage 112 for guiding the first tube 60, a second guide passage 114 for guiding the second tube 62, an auxiliary fixing section 116 for fixing the short third tube 70a, and two pins (holding sections) 118 provided at an outer end portion.

The two pins 118 have an appropriate enlarged-tip shape, and are inserted in end holes of the BC pooling bag 54, thereby fixing the end portions of the BC pooling bag 54. The BC pooling bag 54 has an end portion fixed by the pins 118, and a body portion inserted into the bag hole 105. Each of the pins 118 may have a tip portion split in two, so as to form a narrow slit. Therefore, at the time of fixing the BC pooling bag 54, the pins 118 can be inserted in the end holes by reducing the diameter thereof in a manner of narrowing the slit and, after insertion, the pins 118 can be returned to their initial state, so as to produce a slip-off preventive effect.

The auxiliary fixing section 116 is formed by walls making light contact with both side surfaces of the third tube 70a, and is shaped so as to bend in the direction of an outer diameter thereof, after guiding the third tube 70a in an appropriate amount in the first circumferential direction B1, from an inner diameter side end portion of the BC pooling bag 54. This ensures that, on the third tube 70a, only a sufficiently short tip portion protrudes from the plate section 100 (see FIGS. 7 and 8), and the direction of protrusion is outwards (namely, in the centrifugal direction A1), so that the third tube 70a is not vibrated or moved during centrifugation.

The first guide passage 112 and the second guide passage 114 each has a groove shape, which is formed by walls provided on both sides substantially over the whole length thereof, and which is open on the upper side. The first guide passage 112 and the second guide passage 114 are provided with small slip-off preventive projections 117 at the open upper end portions thereof.

The first guide passage 112 extends in the direction of the inner diameter from an end portion of the BC pooling bag 54, passes through the sensor hole 110, is bent in the first circumferential direction B1 in the vicinity of an inner diameter side end surface, immediately thereafter passes through the first clamp section 106, is bent in the direction of the outer diameter in the vicinity of an end portion in the first circumferential direction B1, and reaches an outer diameter end of the plate section 100, where the first guide passage 112 bends inwards so as to point toward the filter holder 104.

The second guide passage 114 extends in the direction of the inner diameter from the sensor hole 110, is bent in the second circumferential direction B2 in the vicinity of an inner diameter side end surface, immediately thereafter passes through the second clamp section 108, is bent in the direction of the outer diameter in the vicinity of an end portion in the second circumferential direction B2, and thereafter is bent toward a skew lateral side.

Figure 9:
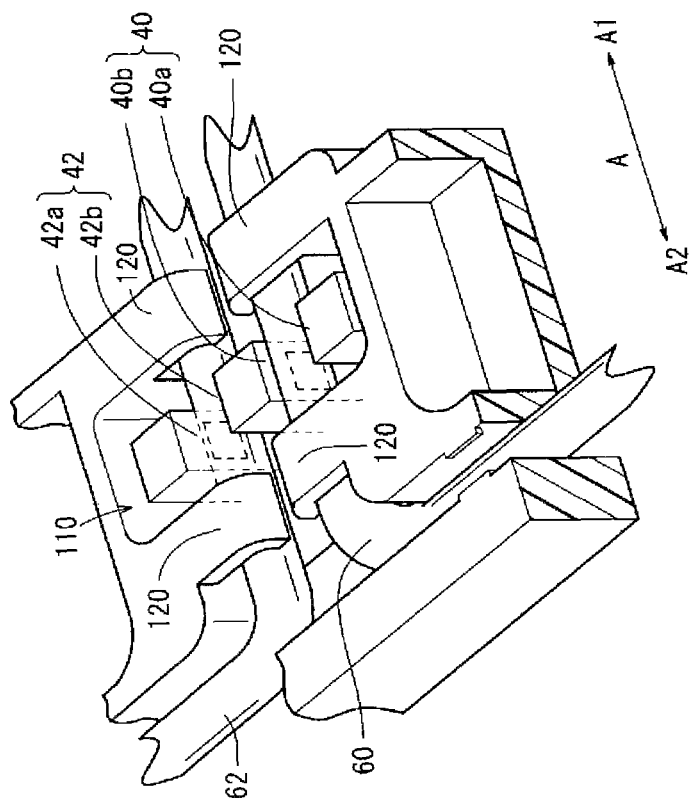
FIG. 9 is a perspective view of the vicinity of a sensor hole in a cassette.

As shown in FIG. 9, in the sensor hole 110, the first tube 60 and the second tube 62 each have upper surfaces thereof fixed stably by two arms 120 having tips bent slightly downwards, and extend respectively in the radial direction. The first tube 60 and the second tube 62 are arranged in parallel in the circumferential direction, in such a manner that gaps are secured at both side surfaces in the circumferential direction of the sensor hole 110, and another gap is secured between the first tube 60 and the second tube 62. When the cassette 50a is mounted on the cassette holder 38, the first sensor 40 and the second sensor 42 are inserted into the gaps in the sensor hole 110, the first tube 60 is disposed between the light emitting section 40a and the light receiving section 40b, and the second tube 62 is disposed between the light emitting section 42a and the light receiving section 42b. The light receiving section 40b and the light receiving section 42b are formed integrally. The first tube 60 and the second tube 62 are held by the four arms 120, so as to remain stable irrespective of the orientation of the cassette 50a. The gap in the circumferential direction between the two arms 120, which are opposed to each other in the circumferential direction, is formed narrowly to such an extent that the first tube 60 and the second tube 62 can pass through the gap in a pressed-down state. As is apparent from FIGS. 7 and 9, the first clamp section 106 and the second clamp section 108 are disposed in the vicinity of the sensor hole 110, and are provided on the downstream side of the first sensor 40 and the second sensor 42.

Figure 10A:
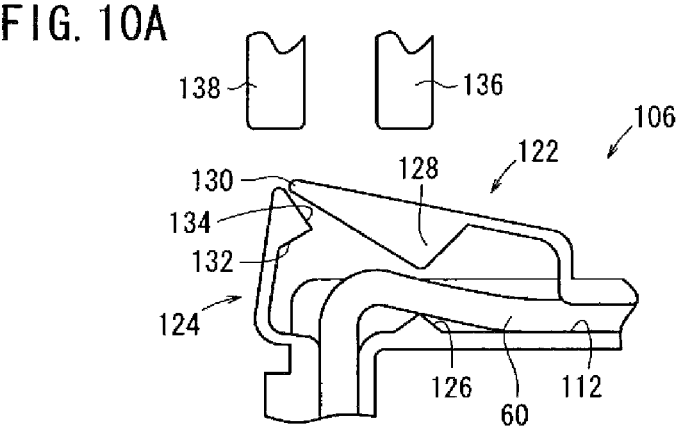
FIG. 10A is a plan view of a first clamp in an initial state.
Figure 10B:
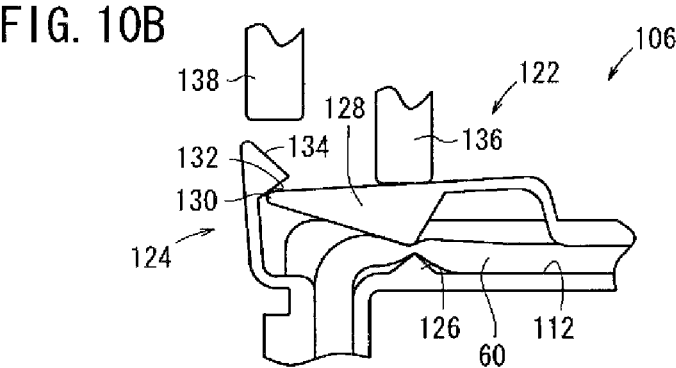
FIG. 10B is a plan view of the first clamp in a closed state.
Figure 10C:
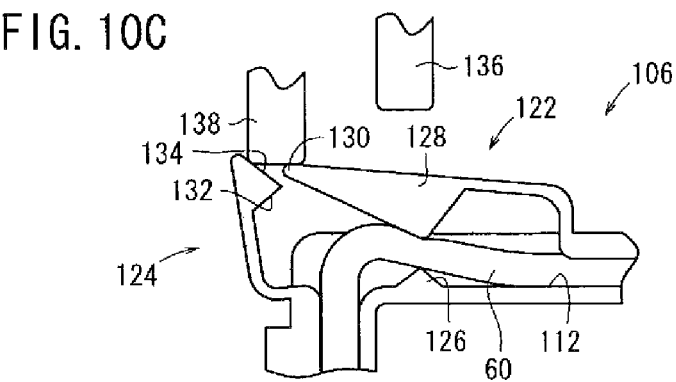
FIG. 10C is a plan view of the first clamp during a returning motion thereof.

As shown in FIGS. 10A to 10C, the first clamp section 106 has a closing section (pressing section) 122, which is provided as part of the first guide passage 112 at a portion on the first circumferential direction B1 side of an inner circumferential end of the plate section 100 and which closes the first tube 60, a latch section 124 for holding the closing section 122 during closure thereof, and a triangular projection 126 provided on a surface on an opposite side from the closing section 122. As illustrated in FIGS. 10A-10C, the pressing section 122 is fixed in a cantilever manner to a portion of the cassette.

The closing section 122 has a bulge portion (pressing portion) 128 for pressing the first tube 60 from a lateral side thereof, and an acute-angular engaged portion 130 provided at the tip of the bulge portion 128. A base portion of the closing section 122 is formed sufficiently small in diameter, so that the bulge portion 128 can be elastically advanced and retracted substantially in the radial direction. The latch section 124 has an engaging portion 132 for engagement with the engaged portion 130 of the bulge section 128 in a state of pressing the first tube 60, and an inclined surface 134 formed at the tip thereof. A direction perpendicular to the inclined surface 134 is oriented toward a skew inner side. Due to the presence of the inclined surface 134, the latch section 124 has a tapered shape when viewed in plan. The latch section 124 is formed with a sufficiently small diameter at the base portion thereof, and can be elastically tilted.

The first clamp section 106 is thus configured simply. In addition, the first clamp section 106 is formed by integral molding with the cassette 50a, so that it is unnecessary to provide the clamp as an independent component part, and a reduction in the number of component parts can be achieved.

As shown in FIG. 10A, in the initial condition of the first clamp section 106, the bulge portion 128 of the closing section 122 is separated from the first tube 60, whereby the first tube 60 is placed in a conducting state.

As shown in FIG. 10B, when the first rod 136 of the central body 14a is extended to press the closing section 122 from a lateral side and to displace the closing section 122, the bulge portion 128 presses down the first tube 60 in cooperation with the projection 126, so as to close the first tube 60. In this instance, the engaged portion 130 engages with the engaging portion 132 by slightly tilting the latch section 124. Thereafter, the closed state of the first tube 60 by the bulge portion 128 is maintained, even after the first rod 136 returns to its original position.

As shown in FIG. 10C, when the second rod 138 is extended, the tip surface thereof slides on the inclined surface 134 and pushes outwardly toward a lateral side, and the latch section 124 is tilted, whereby the engaging portion 132 becomes disengaged from the engaged portion 130, and the engaged state is released. Therefore, when the second rod 138 contracts to its original position, the first clamp section 106 is returned to the initial state shown in FIG. 10A, and the first tube 60 is again placed in a conducting state.

Since the second clamp section 108 is symmetrical with the first clamp section 106, detailed description thereof is omitted. By means of the second clamp section 108, the second tube 62 can be closed and opened. When the blood bag system 10a is mounted on the centrifugation and separation apparatus 11, the first clamp section 106 and the second clamp section 108 are operated by the first clamp driving means 17a and the second clamp driving means 17b of the central body 14a (see FIG. 2). When the blood bag system 10a is not mounted, the first clamp section 106 and the second clamp section 108 can be operated manually.

As shown in FIGS. 7 and 8, the filter holder 104 has a hinge section 140, an attachment 142, and a tube engaging section 144.

Figure 11:
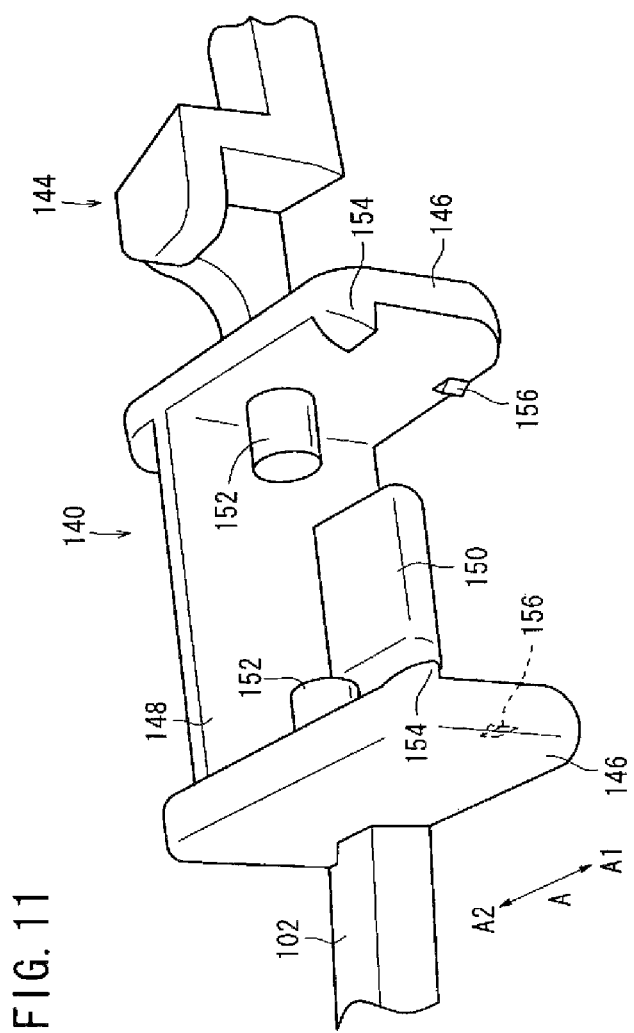
FIG. 11 is a perspective view of a hinge section and a tube engaging section of the cassette.

As shown in FIG. 11, the hinge section 140 is basically composed of a pair of ear pieces 146 opposed to each other in the circumferential direction, and a vertical wall (stopper) 148 provided on the base end side. A thin projection 150 projects in the direction of the outer diameter from the lower end of the vertical wall 148. The vertical wall 148 enables the filter 56 to be set at a more accurate angle.

The pair of ear pieces 146 are provided on inner sides thereof with a pair of round shafts 152 that face toward each other above the projection 150, a pair of small upper stoppers 154 provided at upper end portions on the outer diameter side, and a pair of small ride-over projections 156 provided at lower portions. As is apparent from FIG. 11, the round shafts 152 are constituted by shafts that extend in the circumferential direction, whereby the filter 56 can be tilted with reference to the round shafts 152.

Figure 12:
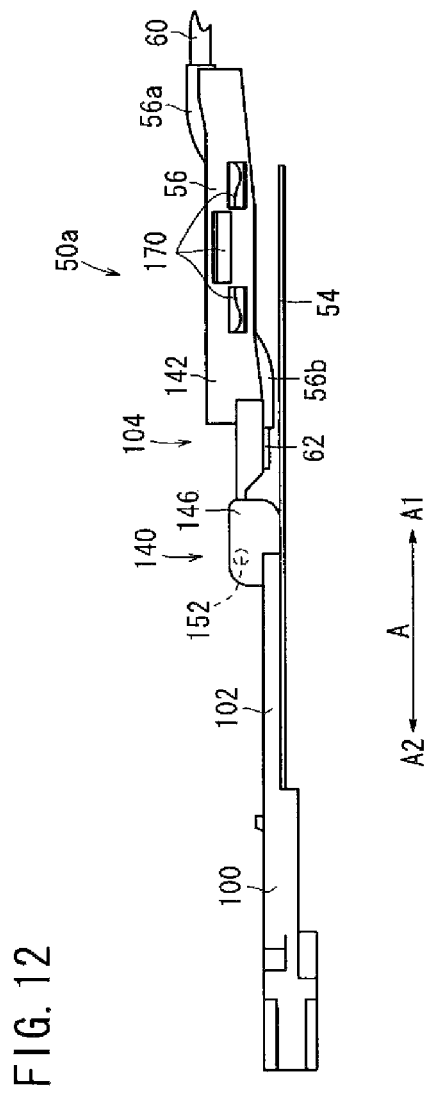
FIG. 12 is a partial enlarged side view of the blood bag system according to the first embodiment, in a condition where the filter holder is expanded.

As shown in FIG. 12, since the round shafts 152 are provided at upper portions of the ear pieces 146, it is possible to move the filter 56, the outlet 56b and the attachment 142 to appropriately high positions in their expanded state. Further, when the assembly is placed on a table surface, such members exert only their own weights on the BC pooling bag 54, and an excessive pressure is not exerted on the BC pooling bag 54.

Figure 13:
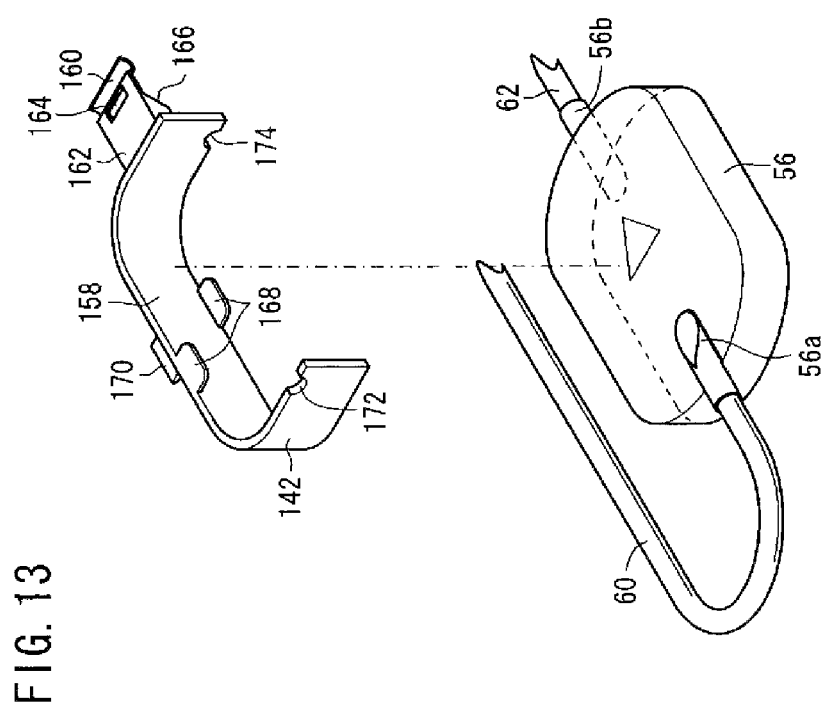
FIG. 13 is an exploded perspective view of a filter and a holder body.

As shown in FIG. 13, the attachment 142 has a support plate 158, which makes contact with and thereby supports one side surface in the longitudinal direction as well as the half upper portion and the half lower portion of the filter holder 104, a hinge turning section 160 having a semicircular arc-like sectional shape that engages with the round shafts 152, and an arm 162 connecting an end portion of the support plate 158 and the hinge turning section 160. The arm 162 includes a quadrilateral hole 164, in which the projection 150 is snugly inserted, and left and right reinforcement plates 166.

The support plate 158 includes a pair of filter holding projections 168 provided on the inside surface so as to hold both surfaces of the filter 56, tube holding projections 170 provided on the outside surface so as to hold the first tube 60 at three positions, a first semicircular notch portion (first fitting portion) 172 provided at an upper tip portion for fitting of the inlet 56a therein, and a second semicircular notch portion (second fitting portion) 174 provided at a lower base end portion for fitting of the outlet 56b therein. In a bent condition, the first semicircular notch portion 172 is disposed on the outer diameter side relative to the second semicircular notch portion 174.

When the attachment 142 is fitted to the hinge section 140, the hinge turning section 160 with the arm 162 directed downward is fitted over the round shafts 152 from a lateral side, and thereafter, the attachment 142 is pushed down by exerting some force thereon, while permitting the arm 162 to ride over the upper stoppers 154. Thus, the attachment 142 is easily mounted in position.

Incidentally, the hinge section 140 is not limited to a shaft-like configuration based on the round shafts 152. For example, a configuration may also be adopted in which a thin section or an elastic section is bent.

A tube engaging section 144 is provided at a portion adjacent to the hinge section 140 of the arch section 102, for thereby holding the second tube 62 in an appropriate orientation.

According to the filter holder 104, the filter 56 can be stably held by the attachment 142, and the first tube 60 and the second tube 62 can be appropriately held by the tube holding projections 170 and the tube engaging section 144.

In addition, when the hinge turning section 160 is turnably supported on the round shafts 152, the attachment 142 and the filter 56 can be tilted into various states, inclusive of an expanded state (see FIG. 7) in which the attachment 142 and the filter 56 are parallel to and substantially in the same plane as the cassette 50a, and a bent state (see FIG. 8) in which the attachment 142 and the filter 56 are bent at an angle of 90° relative to the cassette 50a.

In the expanded (spread) state in which the attachment 142 and the filter 56 are substantially in the same plane as the cassette 50a, further turning thereof is prevented by the upper stoppers 154. Since the upper stoppers 154 are sufficiently small, however, the attachment 142 and the filter 56 may be turned beyond the upper stoppers 154, if necessary, by exerting an appropriate force thereon.

In the condition where the attachment 142 and the filter 56 are bent at 90° relative to the cassette 50a, a side surface of the arm 162 makes surface contact with the vertical wall 148, whereby assured angular positioning is achieved. In this instance, the projection 150 is inserted into the quadrilateral hole 164, whereby stability of the attachment 142 is enhanced. In addition, when an operation is performed to bend the attachment 142, both side portions of the attachment 142 ride over the ride-over projections 156, and an appropriate click feeling is obtained. Therefore, the operator can recognize that the attachment 142 has been set at an appropriate angle.

The tip of the projection 150 may be enlarged in diametral size, so that a more assured click feeling is produced when the projection 150 is inserted into the quadrilateral hole 164, and so that the projection 150 is prevented from slipping off.

According to the aforementioned filter holder 104, at times of storage and transportation of the blood bag system 10a and the like, by placing the attachment 142 and the filter 56 in an expanded state substantially in the same plane as the cassette 50a, the assembly is made sufficiently thin. Accordingly, the assembly can be placed in a vinyl resin bag or the like, together with (for example, in a state of being stacked with) the BC pooling bag 54 and the platelet preserving bag 58. Although such a packed-in-bag state is not shown in the drawings, it is apparent from FIG. 4 that the blood bag system 10a can be contained in a folded state within a vinyl resin bag, which is slightly larger than the platelet preserving bag 58 that makes up the largest of the component parts in area.

Further, when buffy coats are introduced into the BC pooling bag 54 from a required number of BC bags 72, by placing the attachment 142 and the filter 56 in an expanded state substantially in the same plane as the cassette 50a, it is ensured that the system does not expand uselessly, and the system can be easily hung from a girdle stand.

On the other hand, it is preferable for the filter 56 to be preliminarily regulated in orientation when placed in use. Specifically, in order for white blood cells to be removed by the filter 56, the flow direction is set such that the blood component is supplied through the inlet 56a and is guided out through the outlet 56b.

According to the filter holder 104, when the blood bag system 10a is mounted in the centrifugation and separation apparatus 11, the system is used in a condition where the attachment 142 and the filter 56 are bent at 90° relative to the cassette 50a. In addition, as shown in FIG. 8, the filter 56 is held such that the outlet 56b is on a proximal side relative to the hinge section 140, whereas the inlet 56a is on a distal side relative to the hinge section 140. Thus, the filter 56 is used in a condition where the flow direction is oriented against the centrifugal force. As a result, the supernatant liquid 176 flows against the centrifugal force into the filter 56, whereby the flow velocity is suppressed appropriately, and white blood cells can be removed assuredly.

In addition, since the inlet 56a is located below and on the outer diameter side in relation to the outlet 56b, the supernatant liquid 176 having flowed in through the inlet 56a initially collects in a lower portion of the interior of the filter 56, on the outer side of a filter medium 57 (see FIG. 14) disposed in the filter 56, and spreads in the lumen of the filter 56 along an outer diameter side surface while the centrifugal force acts thereon. After the space on the outer side of the filter medium 57 is filled, the supernatant liquid 176 is filtered while passing through the filter medium 57 and is discharged through the outlet 56b. Therefore, the supernatant liquid 176 is filtered while effectively utilizing the entire surface of the filter medium 57 inside the filter 56. Accordingly, white blood cells can be removed more assuredly.

Furthermore, at the time of assembling the filter holder 104, the orientation of the filter 56 is determined by the first semicircular notch portion 172, in which the inlet 56a is fitted, and the second semicircular notch portion 174, in which the outlet 56b is fitted, whereby misassembly can be prevented from occurring.

Next, a method of using the blood bag system 10a and the cassette 50a according to the first embodiment configured in the foregoing manner will be described below.

First, as shown in FIG. 5, the clamp 84 on the third tube 70, the first clamp section 106 and the second clamp section 108 are closed. A required number of BC bags 72 are connected to the branched tube 74, and the container 68 for the platelet preserving liquid is connected to the third tube 70. Buffy coats (or whole blood) collected from different donors are reserved in the BC bags 72, respectively. Then, the buffy coats are collected from the BC bags 72 into the BC pooling bag 54.

Next, on the third tube 70, the clamp 82 is closed whereas the clamp 84 is opened, whereby the platelet preserving liquid is transferred into the BC bags 72, and the platelet preserving liquid is mixed into the buffy coats remaining in the BC bags 72.

Further, the clamp 84 is closed and the clamp 82 is opened, whereby the buffy coats mixed together with the platelet preserving liquid are transferred into the BC pooling bag 54.

The BC pooling bag 54 is pressed by hand, whereby the air inside the BC pooling bag 54 is transferred into the BC bags 72.

Then, the third tube 70 is cut, after being fused and sealed in an anti-leaking manner, at a position near the BC pooling bag 54. The remaining portion forms a short third tube 70a, as shown in FIG. 7, and the third tube 70a is fixed in the auxiliary fixing section 116 so that the tip thereof is oriented in the centrifugal direction. The third tube 70a may be cut shorter than that shown in FIG. 7.

Subsequently, as shown in FIG. 8, the attachment 142 and the filter 56 are bent at 90° relative to the cassette 50a. The filter holder 104 acts to accurately and stably hold the attachment 142 and the filter 56 in a state of being bent at 90°. Since, as mentioned above, the inlet 56a is located below and on the outer diameter side in relation to the outlet 56b when the attachment 142 and the filter 56 are bent at 90° relative to the cassette 50a, the flow velocity is suppressed and the entire surface of the filter medium 57 inside the filter 56 is effectively utilized.

Furthermore, as shown in FIG. 3, the blood bag system 10a is mounted in the insert unit 18. Specifically, the cassette 50a is mounted in the cassette holder 38 and held by the holder projections 45, the BC pooling bag 54 is inserted into the small chamber 30, the filter 56 and the filter holder 104 are inserted into the filter pocket 36, and the platelet preserving bag 58 and the sampling bag 76 are inserted into the large chamber 32. Incidentally, since the filter 56 is maintained quite stably in a state of being bent at 90° by the filter holder 104, a configuration in which the filter pocket 36 is omitted, and the filter 56 and the filter holder 104 are kept in the large chamber 32, may also be adopted, depending on design conditions.

In this case, as shown in FIG. 9, the first tube 60 and the second tube 62 are properly arranged in the sensor hole 110. Therefore, the first tube 60 is appropriately clamped between the light emitting section 40a and the light receiving section 40b of the first sensor 46, whereas the second tube 62 is appropriately clamped between the light emitting section 42a and the light receiving section 42b of the second sensor 42. Naturally, the first tube 60 is not arranged at a detection position of the second sensor 42, and the second tube 62 is not arranged at a detection position of the first sensor 40.

The arch section 102 is stabilized by abutment and mounting thereof on the upper end surface of the wall 34, so that the attachment 142 and the filter 56 suspended from the arch section 102 also are made stable.

In addition, the BC pooling bag 54 is supported by the two pins 118, whereas the first tube 60 connected to the BC pooling bag 54 is fixed along the first guide passage 112. Therefore, the first tube 60 is arranged and oriented in the inner diameter direction A2, as viewed from the BC pooling bag 54.

Next, as shown in FIG. 1, the insert unit 18, with the blood bag system 10a inserted therein, is inserted into the unit insertion hole 16 of the centrifugation and separation apparatus 11. As a result, an end portion of the cassette 50a is fixed by the holding lever 25 (see FIG. 2). In addition, the contacts of the first sensor 40 and the second sensor 42, or interface circuits thereof, are placed in contact with the electrodes 27 (see FIG. 2).

While six insert units 18, basically, are mounted in the centrifugation and separation apparatus 11, the number of insert units 18 may be five or less, so long as the insert units 18 are in balance (preferably, three or two at regular angular intervals).

When the insert unit 18 is inserted into the unit insertion hole 16, the first clamp section 106 and the second clamp section 108 are disposed properly at corresponding positions facing the first clamp driving means 17a and the second clamp driving means 17b (see FIG. 2), respectively. Since the first tube 60 and the second tube 62 are preliminarily arranged properly by the first guide passage 112 and the second guide passage 114 in relation to the first clamp section 106 and the second clamp section 108, the first clamp section 106 and the second clamp section 108 can be properly closed and opened through the first clamp section 106 and the second clamp section 108 under actions of the microcomputer.

Thus, in a series of operations by which the blood bag system 10a and the cassette 50a are mounted, each of the tubes in the blood bag system 10a is preliminarily connected properly. Specifically, by means of the first guide passage 112 and the second guide passage 114 in the cassette 50a, the first tube 60 and the second tube 62 are disposed properly in relation to the sensor hole 110, the first clamp section 106 and the second clamp section 108. Therefore, the operator does not require special knowledge or understanding of operations and procedures for arranging the tubes, whereby the operator can easily and speedily carry out mounting of the blood bag system 10a, without possibility of mismounting. The first tube 60 and the second tube 62 are preliminarily arranged properly within the cassette 50a. In practice, therefore, the operator will be able to mount the blood bag system 10a in the centrifugation and separation apparatus without referring to any manuals or the like.

Next, the cover 12 of the centrifugation and separation apparatus 11 is closed, whereupon a centrifugation step and a separation step (a transfer step) are performed by operating the console section 22.

During automatic operation of the centrifugation and separation apparatus 11, first, the centrifugal drum 14 is rotated to perform the centrifugation step. In this case, the first clamp section 106 and the second clamp section 108 are preliminarily closed. For enhancing security of operation, however, as shown in FIG. 10B, the first rod 136 is extended initially so that the first clamp section 106 is placed in a flat state by the closing section 122. The second clamp section 108 also is placed in a closed state in the same manner.

Figure 14:
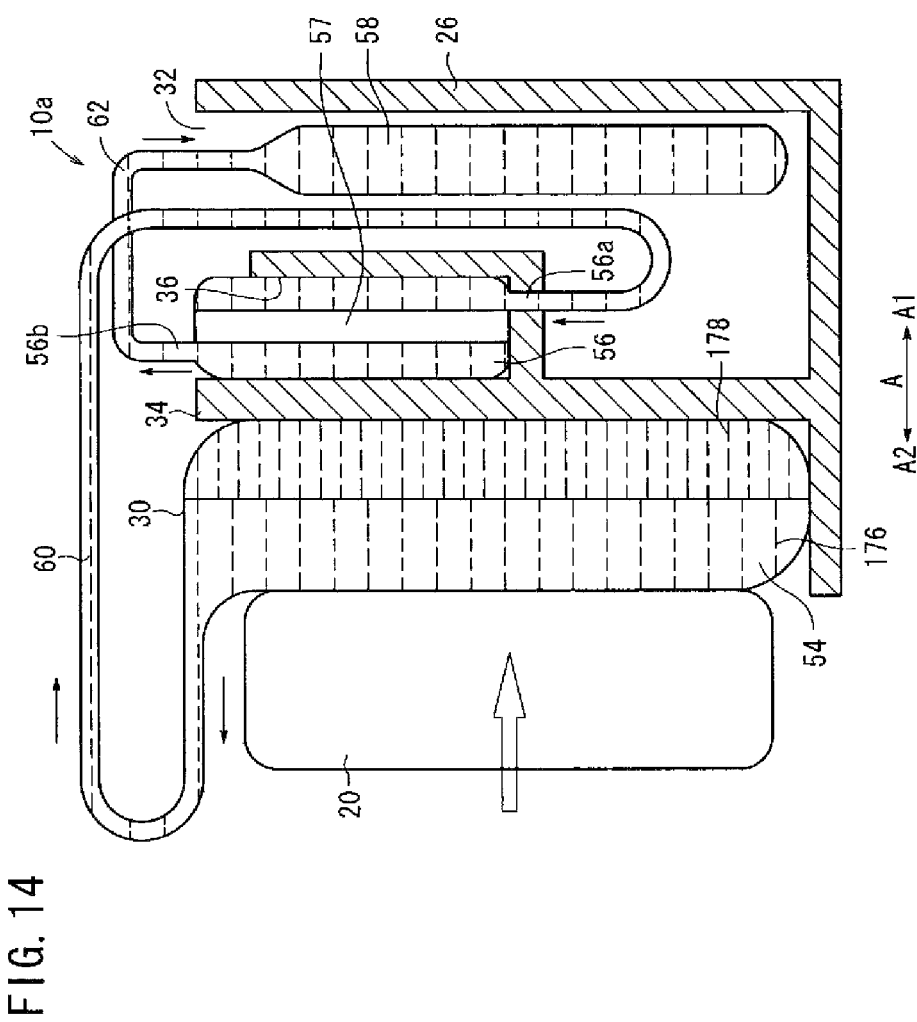
FIG. 14 is a schematic illustration of actions carried out in the centrifugation and separation apparatus.

As shown in FIG. 14, during the centrifugation step, a centrifugal force is imparted to the buffy coat reserved in the BC pooling bag 54 inside the small chamber 30. As a result, the sedimentary liquid 178 containing heavy blood cell components and the like is moved in the direction of the outer diameter, whereas the supernatant liquid 176 containing light platelet components and the like is moved in the direction of the inner diameter, whereby the liquids become separated from each other. The supernatant liquid 176 contains white blood cells. The sedimentary liquid 178 is deep red in color and low in transparency, while the supernatant liquid 176 is constituted by a somewhat yellow-white transparent matter.

The centrifugation and separation apparatus 11 shifts from the centrifugation step to the separation step. During the separation step, while the centrifugal drum 14 continues to rotate, the second rod 138 is extended once as shown in FIG. 10C so as to tilt the latch section 124 and release the engaged state, thereby returning the centrifugation and separation apparatus 11 to the initial condition shown in FIG. 10A and placing the first tube 60 in an open state. The second tube 62 also placed in an open state in the same manner.

Next, as shown in FIG. 14, the presser 20 is displaced in the centrifugal direction A1 so as to press the BC pooling bag 54. The internal volume of the BC pooling bag 54 is reduced while being clamped between the presser 20 and the wall 34, whereby the liquid contained therein is discharged through the first tube 60. In this instance, in the interior of the BC pooling bag 54, the sedimentary liquid 178 is collected in the direction of the outer diameter, while the supernatant liquid 176 is collected in the direction of the inner diameter. Meanwhile, the first tube 60 is oriented in the direction of the inner diameter, so that only the supernatant liquid 176 is ejected into the first tube 60.

The supernatant liquid 176 that is ejected into the first tube 60 flows past the location of the first clamp section 106, which is in an open state, whereupon white blood cells are removed therefrom by the filter 56. In this instance, since the filter 56 is set so that the inlet 56a is located below and on the outer diameter side relative to the outlet 56b, the supernatant liquid 176 flows in a direction resistant to gravity and centrifugal force. Therefore, the flow velocity of the supernatant liquid 176 is suppressed, and removal of white blood cells can be achieved assuredly through effective utilization of the entire surface of the filter medium 57. The supernatant liquid 176 having passed through the filter 56 flows past the location of the second clamp section 108, which is in an open state, and is supplied into and reserved within the platelet preserving bag 58.

It is desirable that the supernatant liquid 176 in the BC pooling bag 54 be transferred into the platelet preserving bag 58 as completely as possible. However, it is undesirable for the sedimentary liquid 178 to be transferred into the platelet preserving bag 58. In view of this, the liquids that pass through the first tube 60 and the second tube 62 are monitored by the first sensor 40 and the second sensor 42, and a control is carried out in order to prevent the sedimentary liquid 178 from being transferred into the platelet preserving bag 58.

Specifically, the microcomputer monitors signals supplied thereto from the first sensor 40 and the second sensor 42, determines transparency values of the liquids that pass through the first tube 60 and the second tube 62 based on the magnitudes of the signals, and distinguishes the supernatant liquid 176 and the sedimentary liquid 178 from each other by their respective transparencies.

When the BC pooling bag 54 is pressed by the presser 20 during the separation step, the supernatant liquid 176 is guided out into the first tube 60 at a beginning period, so it can be confirmed by the first sensor 40 and the second sensor 42 that the supernatant liquid 176 is flowing therein due to the transparency of the liquid.

While pressing of the BC pooling bag 54 by the presser 20 is continued, the supernatant liquid 176 in the BC pooling bag 54 flows out completely, and thereafter, the sedimentary liquid 178 is guided out. As a result, at first, the first sensor 40 detects that the liquid flowing through the first tube 60 is changed into the sedimentary liquid 178. At this point in time, the separation step may be considered finished. In order to collect the platelets into the platelet preserving bag 58 as much as possible, however, it is desirable that portions of the supernatant liquid 176, which remain in the first tube 60 and the second tube 62, also are fed out into the platelet preserving bag 58. From this point of view, after the sedimentary liquid 178 has been detected by the first sensor 40, pressing by the presser 20 may be further continued for a predetermined period of time.

Next, upon elapse of a predetermined time period, when it has been detected by the second sensor 42 that the liquid flowing through the second tube 62 has changed into the sedimentary liquid 178, the first rods 136 are extended (see FIG. 10B) in order to close the first clamp section 106 and the second clamp section 108, thereby placing the first tube 60 and the second tube 62 in a closed state. Further, the centrifugal drum 14 is stopped, whereupon the separation step is finished.

Upon elapse of a predetermined period of time from detection of the sedimentary liquid 178 by the first sensor 40, the sedimentary liquid 178 reaches the filter 56, and portions of the supernatant liquid 176 which remain in the first tube 60 and the second tube 62 are fed out into the platelet preserving bag 58 accordingly. Incidentally, before the predetermined time period has lapsed, basically, the sedimentary liquid 178 will not reach the position of the second sensor 42 (namely, the position of the sensor hole 110). In order to prevent the sedimentary liquid 178 from mixing into the platelet preserving bag 58, however, monitoring thereof by the second sensor 42 is performed.

Immediately upon detection by the second sensor 42 of transfer of the sedimentary liquid 178 into the second tube 62, the first clamp section 106 and the second clamp section 108 are simultaneously placed in a closed state, so as to prevent the sedimentary liquid 178 from flowing further downstream. There is a slight time lag until the first clamp section 106 and the second clamp section 108 become fully closed after detection of the sedimentary liquid 178 by the second sensor 42. In the course of the second tube 62, however, the second clamp section 108 is located on a downstream side relative to the position of the sensor hole 110, where the second sensor 42 is provided. Therefore, the sedimentary liquid 178 does not flow to the downstream side of the second clamp section 108. Even if the sedimentary liquid 178 flows past the position of the second clamp section 108, the sedimentary liquid 178 will not reach the platelet preserving bag 58, because a certain distance is provided between the position of the second clamp section 108 and the platelet preserving bag 58.

When the separation step is finished, and the centrifugal drum 14 is stopped completely in this manner, the cover 12 is opened. The insert units 18 are taken out by operating the holding levers 25, and the blood bag systems 10a are taken out by detaching the cover bodies 28. In this case, the cassette 50a can easily be detached from the cassette holder 38 simply by operating the detaching levers 44 (see FIG. 3).

Further, the first tube 60 in the blood bag system 10a is cut after being fused at a position near the BC pooling bag 54, whereby the BC pooling bag 54 serves as a blood product containing blood cell components. On the other hand, when the second tube 62 is cut after being fused at a position near the platelet preserving bag 58, the platelet preserving bag 58 serves as a blood product containing platelets. The blood product of the platelet preserving bag 58 permits a portion thereof to be transferred into the sampling bag 76, and to be served to a predetermined test or the like.

According to the blood bag system 10a and the cassette 50a of the first embodiment, as mentioned above, the cassette 50a has the first tube 60 and the second tube 62 preliminarily arranged properly therein, so that it is sufficient simply to mount the cassette 50a into the central body 14a of the centrifugation and separation apparatus 11. Therefore, the need for intricate laying and arrangement of the first tube 60 and the second tube 62, as well as the need for arranging the first clamp section 106 and the second clamp section 108, are eliminated, and mounting can be carried out easily and assuredly. In addition, the cassette 50a includes the first clamp section 106 and the second clamp section 108, which are disposed properly in relation to the first clamp driving means 17a and the second clamp driving means 17b within the centrifugation and separation apparatus 11.

In addition, since the first clamp section 106 and the second clamp section 108 are formed by integral molding with the cassette 50a, the first clamp section 106 and the second clamp section 108 can be configured easily, and such integral molding enables a reduction in the number of component parts. Naturally, the operator does not need to mount the first clamp section 106 and the second clamp section 108 to the cassette 50a, so that the required procedure is simple and there is no fear of misarrangement.

The cassette 50a is fixed to the centrifugation and separation apparatus 11 such that the first tube 60 and the second tube 62 are partially set horizontally and oriented in the radial direction, and so that the blood components inside the tubes flow in the direction of the inner diameter. In these parts, the blood components flow against centrifugal force, so that the flow velocities thereof can be prevented from increasing excessively.

Further, the first tube 60 and the second tube 62 cross the sensor hole 110 on the upper side and in a radial direction, while being located to enable detection thereof by the first sensor 40 and the second sensor 42. Thus, the liquids inside the first tube 60 and the second tube 62 can be detected reliably.

The two pins 118, which serve as a holding section for the cassette 50a, hold an end portion where the first tube 60 of the first bag is provided. As a result, the first tube 60 is oriented in the direction of the inner diameter, and the supernatant liquid 176, which is collected in the direction of the inner diameter by the centrifugation step, can be transferred from the first tube 60 during the separation step.

The cassettes 50a each have the first clamp section 106 and the second clamp section 108 arranged in parallel with each other in the circumferential direction, on a side pointing toward the center of rotation of the centrifugal drum 14 of the centrifugation and separation apparatus 11, whereby the first clamp driving means 17a and the second clamp driving means 17b can be arranged in a concentrated manner within the central body 14a at the rotating section. In addition, with the first clamp section 106 and the second clamp section 108 arranged side by side in the circumferential direction, the surface on the rotational center side of the cassette 50a is utilized effectively, and good balance is secured. Further, with the first clamp section 106 and the second clamp section 108 arranged in parallel with each other in the circumferential direction, the cassette 50a forms a single layer in which overlapping of the first tube 60 with the second tube 62 does not occur at any location, and further, the cassette 50a has a simple structure such that arrangement of the first tube 60 and the second tube 62 during the manufacturing stage is easy to carry out.

Since the cassette 50a includes the attachment 142 by which the filter 56 is held so as to be changed in orientation, orientations of the filter 56 during storage and during use thereof can be changed appropriately.

The blood bag system 10a and the cassette 50a are inexpensive configurations, which are suitable for disposable use.

Assembly, packaging and a sterilizing treatment of the blood bag system 10a are performed under a predetermined quality control by the manufacturer. The blood bag system 10a is assembled by a predetermined automatic machine, or is assembled manually by use of predetermined assembly jigs. Further, tests are preliminarily conducted by predetermined automatic testers, whereby an assured arrangement can be achieved.

Next, a blood bag system 10b and a cassette 50b according to a second embodiment will be described below. Components of the blood bag system 10b (and each of 10c and 10d) and the cassette 50b (and each of 50c and 50d), which are the same as those of the above-described blood bag system 10a and cassette 50a, are denoted by the same reference characters used above, and detailed descriptions of such features are omitted.

The blood bag system 10b includes the cassette 50b and a multiple bag 52. The multiple bag 52 is basically the same as that used in the blood bag system 10a, except that a first tube 60 and a second tube 62 are provided together with a first clamp 200 and a second clamp 202.

Figure 15:
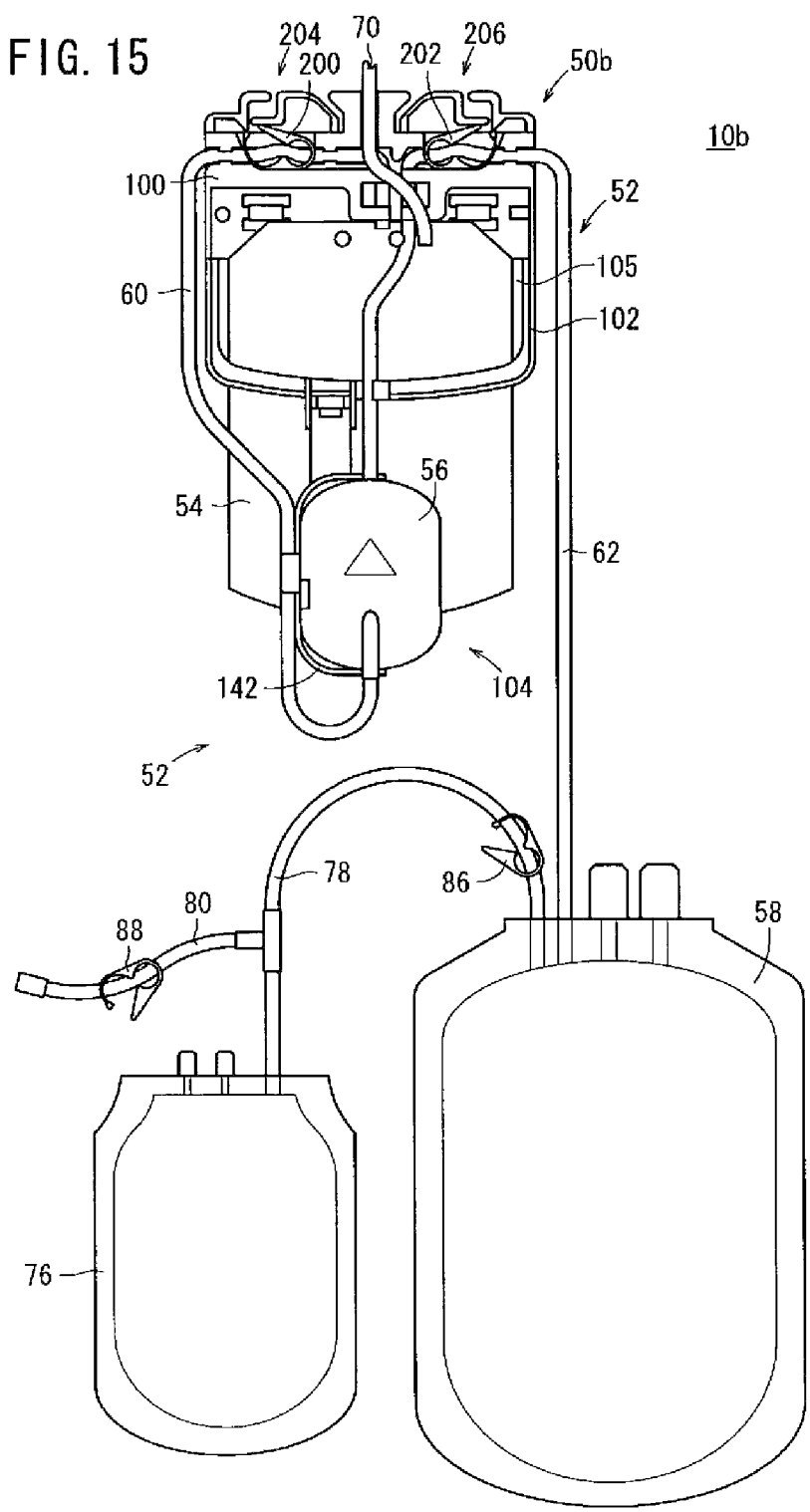
FIG. 15 is a partial enlarged plan view of a blood bag system according to a second embodiment of the invention.
Figure 16:
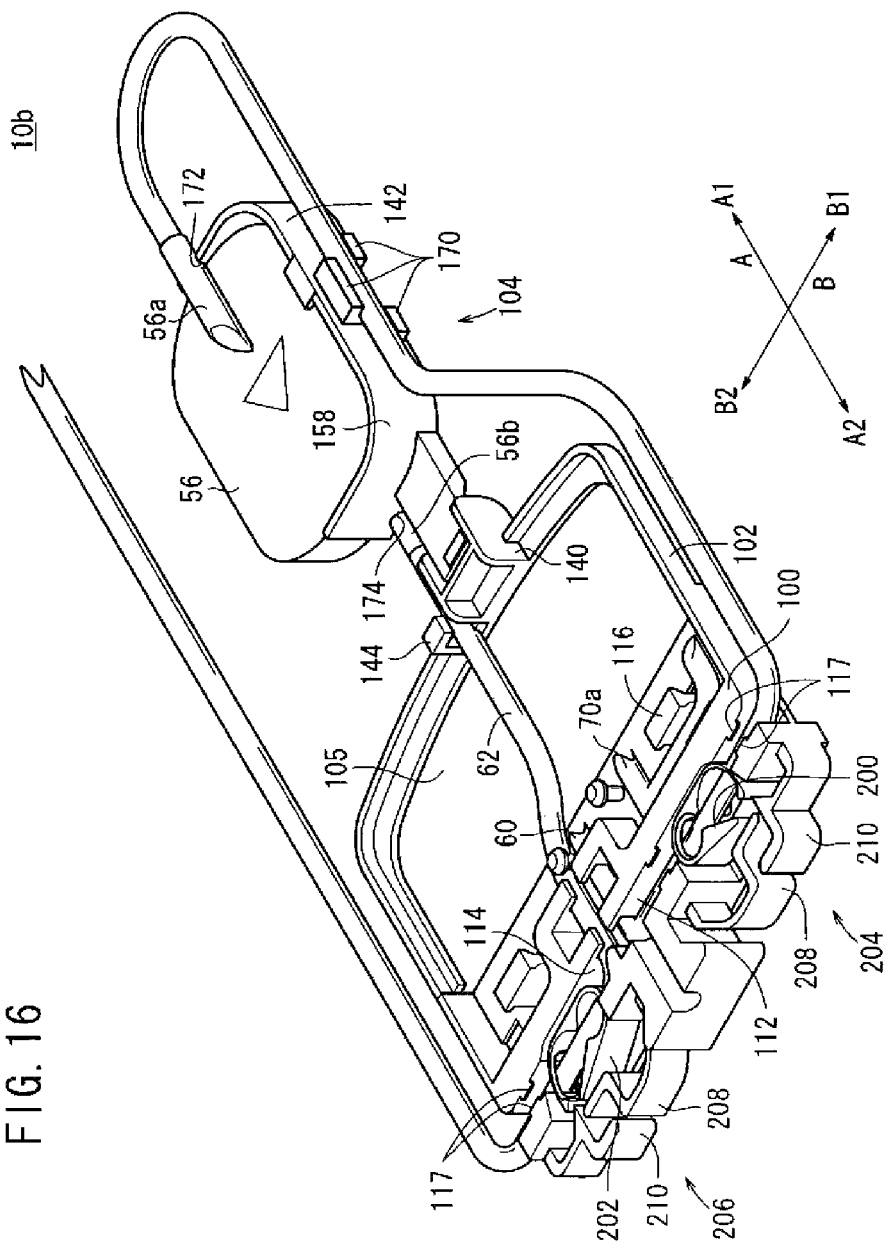
FIG. 16 is a partial enlarged perspective view of the blood bag system according to the second embodiment, in a condition where a filter holder is not bent.

As shown in FIGS. 15 and 16, in place of the above-described first clamp section 106 and second clamp section 108 (see FIG. 4), the blood bag system 10b has the first clamp 200 and the second clamp 202, as well as a first clamp operating section 204 and a second clamp operating section 206, for operating and placing the first clamp 200 and the second clamp 202 in closed and open states.

The first clamp 200 and the second clamp 202 make up means for closing and opening intermediate portions of the first tube 60 and the second tube 62, similar to the above-described first clamp section 106 and second clamp section 108.

Figure 17:
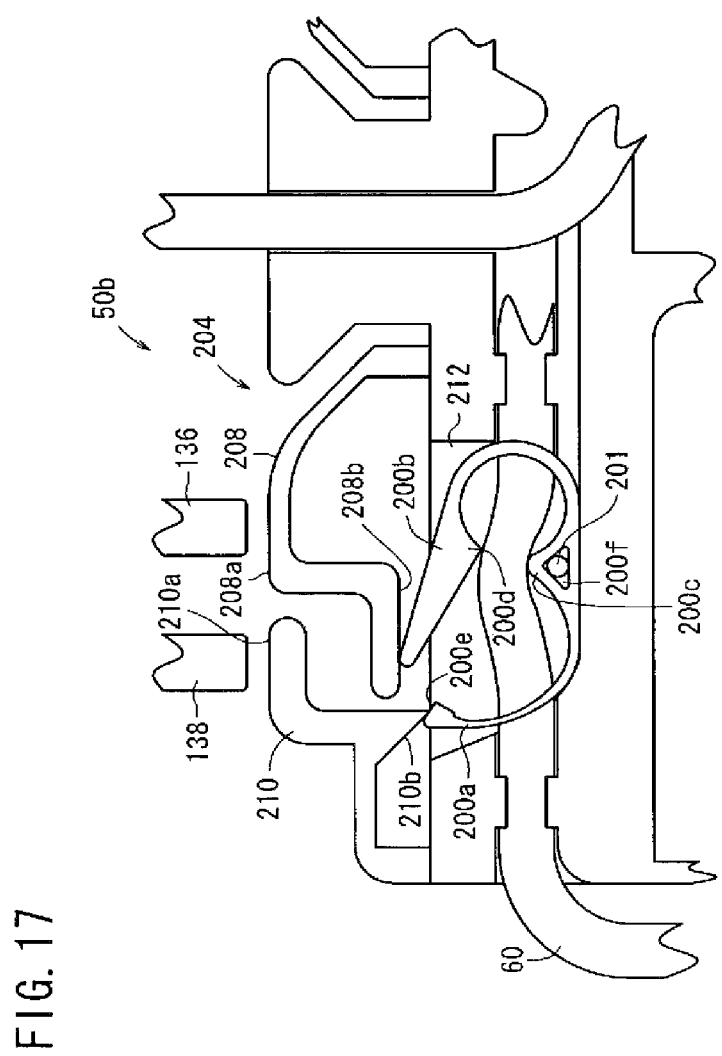
FIG. 17 is a plan view of a first clamp operating section.

As shown in FIG. 17, the first clamp 200 is a resin body provided at one end thereof with a latch section 200a, which is short and bent back in a J-shape, and provided at the other end thereof with a closing section (pressing section) 200b, which is somewhat longer and bent back in a U-shape. The first clamp 200 further is provided at an inside surface thereof with a projection 200c, and at both ends thereof with holes in which to insert the first tube 60. The projection 200c is located at a position slightly deviated from the center, and has a hole 200f therein. In an initial state, the closing section 200b is opened to an appropriate degree.

The latch section 200a, the closing section 200b and the projection 220c correspond respectively to the latch section 124, the closing section 122 and the projection 126 described above (see FIG. 10A). More specifically, when the closing section 200b is pushed in toward the inner side, the first tube 60 can be closed by a bulge portion 200d on the inside of the closing section 200b and the projection 200c, while the closing section 200b is held by the latch section 200a.

When an inclined surface 200e at the tip of the latch section 200a is pushed toward a lateral side (or if the inclined surface 200e is pushed by a rod or the like from a lateral side) and the latch section 200a is thereby tilted toward the lateral side, the closing section 200b is released from an engaged state and returns to its original position, thereby opening the first tube 60.

The second clamp 202 has the same structure as the first clamp 200. As for the first clamp 200 and the second clamp 202, the same structures as in the above-mentioned clamp 82, 84, 86, 88 can be used.

The first clamp operating section 204 in the cassette 50b includes a first pressing section 208 for pushing in the closing section 200b by operation of a first rod 136, and a second pressing section 210 that slides on an inclined surface 200e by operation of a second rod 138, so as to tilt the latch section 200a toward a lateral side. The first pressing section 208 and the second pressing section 210 are thinned in the vicinity of base end portions thereof so as to have elasticity, and the first pressing section 208 and the second pressing section 210 can be elastically displaced substantially in the radial direction under operations of the first rod 136 and the second rod 138. End faces, on an inner diametrical side of the first pressing section 208 and the second pressing section 210, are formed as outside flat surfaces 208a and 210a substantially along the circumferential direction, so that such end faces are stably pressed by the first rod 136 and the second rod 138.

The first pressing section 208 is provided with an inside flat surface 208b substantially along the circumferential direction, so as to be capable of easily pressing an inner diameter side portion of a tip portion of the closing section 200b. The second pressing section 210 is provided with an inclined surface 210b, which is suitable for sliding along the inclined surface 200e of the latch section 200a.

The first clamp operating section 204 is provided with a clamp space 212 in which the first clamp 200 is held, while leaving a small gap. The clamp space 212 is shaped such that the first clamp 200 cannot be mounted therein in an erroneously deviated position, or in a reverse orientation. Specifically, the clamp space 212 is provided with a projection (columnar section) 201 that is inserted into the hole 200f, whereby positioning of the first clamp 200 is achieved. Since the projection 200c and the hole 200f are each located at a position slightly deviated from the center, there is no possibility of the first clamp 200 being mounted in a reverse orientation. Within the clamp space 212, a gap is secured, which permits the latch section 200a to be tilted toward a lateral side.

The second clamp operating section 206 is symmetrical in shape with the first clamp operating section 204. The first clamp operating section 204 and the second clamp operating section 206 can be operated respectively by the first clamp driving means 17a and the second clamp driving means 17b (see FIG. 2), and can be operated manually when the blood bag system 10b is not mounted within the centrifugation and separation apparatus 11.

A first guide passage 112 and a second guide passage 114 in the cassette 50b of the blood bag system 10b are shorter than those in the above-described blood bag system 10a. The first guide passage 112 and the second guide passage 114 are formed so as to extend through upper portions of a sensor hole 110, to thereby guide the first tube 60 in a first circumferential direction B1, and the second tube 62 in a second circumferential direction B2.

In the blood bag system 10b and the cassette 50b configured as described above, the first tube 60 and the second tube 62 are preliminarily arranged properly, similar to the above-described blood bag system 10a and cassette 50a. Therefore, it is sufficient for the cassette 50b to be mounted within the central body 14a of the centrifugation and separation apparatus 11, and the need for intricate laying and arrangement of the first tube 60 and the second tube 62 is eliminated, so that mounting thereof can be carried out easily and assuredly. In addition, the cassette 50b includes the first clamp 200, the second clamp 202, the first clamp operating section 204, and the second clamp operating section 206, with such components being arranged properly in relation to the first clamp driving means 17a and the second clamp driving means 17b (see FIG. 2) of the centrifugation and separation apparatus 11.

In the blood bag system 10b and the cassette 50b, conventionally used general-purpose clamp can be applied to the first clamp 200 and the second clamp 202 arranged, so that the operator can easily comprehend the clamping means during manual operation thereof. Further, in the case where the multiple bag 52 must be detached from the cassette 50b for some reason, the first tube 60 and the second tube 62 can be kept closed by the first clamp 200 and the second clamp 202.

Figure 18:
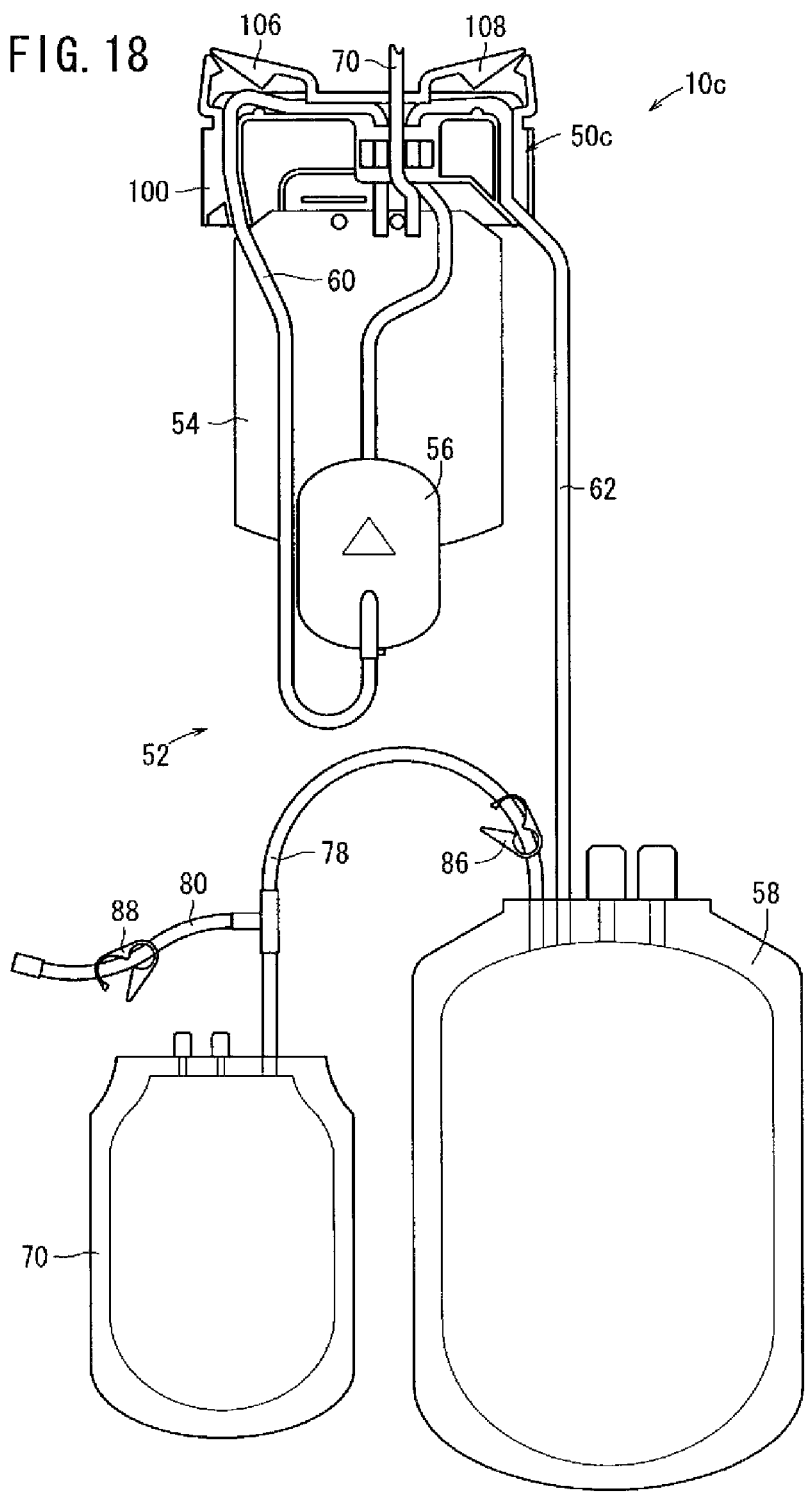
FIG. 18 is a partial enlarged plan view of a blood bag system according to a third embodiment of the invention.

As shown in FIG. 18, a blood bag system 10c and a cassette 50c according to a third embodiment have respective configurations, which are obtained by omitting the arch section 102 and the filter holder 104 from the above-described blood bag system 10a and cassette 50a.

Figure 19:
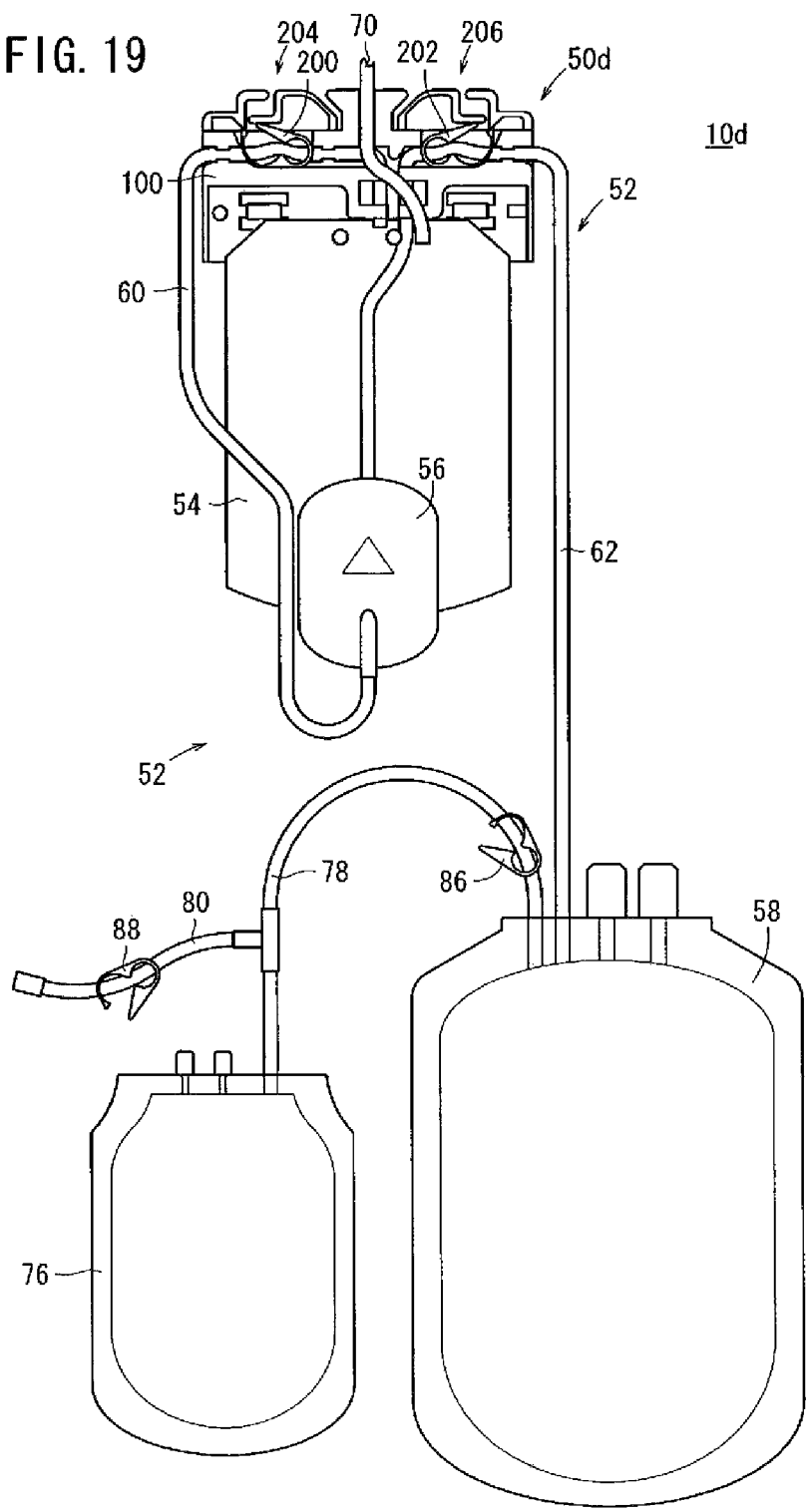
FIG. 19 is a partial enlarged plan view of a blood bag system according to a fourth embodiment of the invention.

As shown in FIG. 19, a blood bag system 10d and a cassette 50d according to a fourth embodiment have respective configurations, which are obtained by omitting the arch section 102 and the filter holder 104 from the above-described blood bag system 10b and cassette 50b.

Omission of the filter holder 104 permits the cassettes 50c, 50d to be simpler in configuration. In this case, the filter 56 can be maintained in a proper attitude by the filter pocket 36.

The blood bag systems 10c, 10d and the cassettes 50c, 50d have the same operational effects as those of the above-described blood bag system 10a and cassette 50a.

The blood bag systems 10a to 10d and the cassettes 50a to 50d are applicable not only to a centrifugation and separation apparatus 11, but also to a blood component collection apparatus, a whole blood collection apparatus, an automatic blood separation apparatus, etc. The liquid reserved in the BC pooling bag 54 is not limited to a buffy coat, and depending on the use thereof, whole blood (contained liquid) may be reserved therein.

The blood bag system and the cassette according to the present invention are not limited to the above-described embodiments, and it is a matter of course that various configurations could be adopted without deviating from the essence and gist of the invention.

The invention claimed is:

1. A blood bag system comprising:
a first bag for reserving whole blood or a blood component;
a filter having a filter medium for removing predetermined cells from a blood component obtained by centrifugation of the liquid contained in the first bag;
a second bag for reserving a blood component obtained upon removal of the predetermined cells by the filter;
a first tube connecting the first bag and an inlet of the filter;
a second tube connecting the second bag and an outlet of the filter;
a cassette comprising a first guide passage holding a part of the first tube and a second guide passage holding a part of the second tube;
wherein the cassette has a first clamp section which is integrally molded with the cassette and is movable relative to the first guide passage and toward the part of the first tube held in the first guide passage to close the first tube and movable relative to the first guide passage away from the part of the first tube held in the first guide passage to open the first tube, the cassette also having a second clamp section which is integrally molded with the cassette and is movable relative to the second guide passage and toward the part of the second tube held in the second guide passage to close the second tube and movable relative to the second guide passage away from the part of the second tube held in the second guide passage to open the second tube, the first clamp section being different from the first and second guide passages, and the second clamp section being different from the first and second guide passages; and
wherein the first clamp section and the second clamp section are in a common plane.

2. A blood bag system comprising:
a first bag for reserving whole blood or a blood component;
a filter having a filter medium for removing predetermined cells from a blood component obtained by centrifugation of the liquid contained in the first bag;
a second bag for reserving a blood component obtained upon removal of the predetermined cells by the filter;
a first tube connecting the first bag and an inlet of the filter;
a second tube connecting the second bag and an outlet of the filter;
a first clamp movable in a plane toward the first tube to press against and close the first tube and movable in the plane away from the first tube to be spaced from and open the first tube;
a second clamp movable in the plane toward the second tube to press against and close the second tube and movable in the plane away from the second tube to be spaced from and open the second tube;
a cassette for holding a part of the first tube, a part of the second tube, the first clamp and the second clamp;
wherein the cassette has a first clamp operating section different from the first and second clamps and movable in the plane relative to the first clamp for operating the first clamp to move the first clamp in the plane toward the first tube to a position in which the first clamp presses against and closes the first tube, the cassette also having a second clamp operating section different from the first and second clamps and movable in the plane relative to the second clamp for operating the second clamp to move the second clamp in the plane toward the second tube to a position in which the second clamp presses against and closes the second tube;
the first clamp operating section including an elastic portion possessing elasticity so that a force applied to the first clamp operating section results in the portion of the first clamp operating section being elastically displaced toward the first clamp to operate the first clamp toward the first tube to the position in which the first clamp presses against and closes the first tube;
the second clamp operating section including an elastic portion possessing elasticity so that a force applied to the second clamp operating section results in the portion of the second clamp operating section being elastically displaced toward the second clamp to operate the second clamp toward the second tube to the position in which the second clamp presses against and closes the second tube; and
wherein the first clamp and the second clamp are in a common plane.

3. The blood bag system according to claim 2, wherein the first clamp operating section and the second clamp operating section are configured integrally with the cassette.

4. The blood bag system according to claim 2, wherein the first clamp and the second clamp are arranged in parallel within the cassette.

5. The blood bag system according to claim 1, wherein whole blood or a blood component collected from a plurality of donors is reserved in the first bag, and
the blood bag system is mounted in a centrifugation and separation apparatus for centrifuging the liquid contained in the first bag into a supernatant liquid and a sedimentary liquid, removing a predetermined component from the supernatant liquid by the filter, and for transferring the supernatant liquid, deprived of the predetermined component, into the second bag.

6. The blood bag system according to claim 1, wherein a centrifugation and separation apparatus includes a first sensor and a second sensor, each of which has a light emitting section and a light receiving section, and which detects the kind of liquid passing between the light emitting section and the light receiving section,
the cassette has a sensor hole in which the first sensor and the second sensor are inserted, and
the first tube is located so as to pass between the light emitting section and the light receiving section of the first sensor, whereas the second tube is located so as to pass between the light emitting section and the light receiving section of the second sensor.

7. A cassette mounted to a multiple bag comprising:
a first bag for reserving whole blood or a blood component;
a filter having a filter medium for removing predetermined cells from a blood component obtained by centrifugation of the liquid contained in the first bag;
a second bag for reserving a blood component obtained upon removal of the predetermined cells by the filter;
a first tube connecting the first bag and an inlet of the filter;
a second tube connecting the second bag and an outlet of the filter;
wherein the cassette holds a part of the first tube in a first guide passage and a part of the second tube in a second guide passage, the cassette including a first clamp section integrally molded with the cassette and movable relative to the first guide passage and toward the part of the first tube held in the first guide passage to press against the first tube and close the first tube and movable relative to the first guide passage away from the part of the first tube held in the first guide passage and out of pressing contact with the first tube to open the first tube, the cassette also including a second clamp section integrally molded with the cassette and movable relative to the second guide passage and toward the part of the second tube held in the second guide passage to press against the second tube and close the second tube and movable relative to the second guide passage away from the part of the second tube held in the second guide passage and out of pressing contact with the second tube to open the second tube, the first clamp section being different from the first and second guide passages, and the second clamp section being different from the first and second guide passages; and
wherein the first clamp section and the second clamp section are in a common plane.

8. A cassette mounted to a multiple bag comprising:
a first bag for reserving whole blood or a blood component;
a filter having a filter medium for removing predetermined cells from a blood component obtained by centrifugation of the liquid contained in the first bag;
a second bag for reserving a blood component obtained upon removal of the predetermined cells by the filter;
a first tube connecting the first bag and an inlet of the filter;
a second tube connecting the second bag and an outlet of the filter;
a first clamp movable in a plane toward the first tube to press against and close the first tube and movable in the plane away from the first tube to be spaced from and open the first tube;
a second clamp movable in the plane toward the second tube to press against and close the second tube and movable in the plane away from the second tube to be spaced from and open the second tube;
wherein the cassette holds a part of the first tube, a part of the second tube, the first clamp and the second clamp, the cassette including a first clamp operating section different from the first and second clamps, the first clamp operating section comprising a first pressing section and a second pressing section that are spaced apart from one another, the first pressing section being movable in the plane relative to the first clamp upon application of a force to the first pressing section for operating the first clamp to move the first clamp in the plane toward the first tube and into pressing contact with the first tube so that the first clamp closes the first tube and flow through the first tube is prevented, the second pressing section being movable in the plane relative to the first clamp upon application of a force to the second pressing section for operating the first clamp to move the first clamp in the plane to release the pressing contact of the first clamp against the first tube so that flow through the first tube is permitted;
the cassette also including a second clamp operating section different from the first and second clamps, the second clamp operating section comprising a first pressing section and a second pressing section that are spaced apart from one another, the first pressing section of the second clamp operating section being movable in the plane relative to the second clamp upon application of a force to the first pressing section of the second clamp operating section for operating the second clamp to move the second clamp in the plane toward the second tube and into pressing contact with the second tube so that the second clamp closes the second tube and flow through the second tube is prevented, the second pressing section of the second clamp operating section being movable in the plane relative to the second clamp upon application of a force to the second pressing section of the second clamp operating section for operating the second clamp to move the second clamp in the plane to release the pressing contact of the second clamp against the second tube so that flow through the second tube is permitted; and
wherein the first clamp and the second clamp are in a common plane.

9. The blood bag system according to claim 2, wherein whole blood or a blood component collected from a plurality of donors is reserved in the first bag, and
the blood bag system is mounted in a centrifugation and separation apparatus for centrifuging the liquid contained in the first bag into a supernatant liquid and a sedimentary liquid, removing a predetermined component from the supernatant liquid by the filter, and for transferring the supernatant liquid, deprived of the predetermined component, into the second bag.

10. The blood bag system according to claim 3, wherein a centrifugation and separation apparatus includes a first sensor and a second sensor, each of which has a light emitting section and a light receiving section, and which detects the kind of liquid passing between the light emitting section and the light receiving section,
the cassette has a sensor hole in which the first sensor and the second sensor are inserted, and
the first tube is located so as to pass between the light emitting section and the light receiving section of the first sensor, whereas the second tube is located so as to pass between the light emitting section and the light receiving section of the second sensor.

11. The blood bag system according to claim 2, wherein the cassette includes a first clamp space and a second clamp space that are spaced apart from one another, the first clamp being positioned in the first clamp space and the second clamp being positioned in the second clamp space.

12. The cassette according to claim 8, wherein the cassette includes a first clamp space and a second clamp space that are spaced apart from one another, the first clamp being positioned in the first clamp space and the second clamp being positioned in the second clamp space.

13. The blood bag system according to claim 1, wherein the cassette possesses oppositely facing first and second surfaces, and an outer edge defining an outer periphery of the first and second surfaces of the cassette, the first and second guide passages both being located at the first surface of the cassette and both opening in a common direction.

14. The blood bag system according to claim 1, wherein the first clamp section is movable in a plane toward the first tube to press against and close the first tube and is movable in the plane away from the first tube to be spaced from and open the first tube, and wherein the second clamp section is movable in the plane toward the second tube to press against and close the second tube and is movable in the plane away from the second tube to be spaced from and open the second tube.

15. A blood bag system comprising:
 a first bag for reserving whole blood or a blood component;
 a filter having a filter medium for removing predetermined cells from a blood component obtained by centrifugation of the liquid contained in the first bag;
 a second bag for reserving a blood component obtained upon removal of the predetermined cells by the filter;
 a first tube connecting the first bag and an inlet of the filter;
 a second tube connecting the second bag and an outlet of the filter; and
 a cassette comprising a plate section, the plate section possessing a first guide passage holding a part of the first tube and a second guide passage holding a part of the second tube, wherein the cassette has a first clamp section movable relative to the first guide passage and toward the part of the first tube held in the first guide passage to close the first tube and movable relative to the first guide passage away from the part of the first tube held in the first guide passage to open the first tube, the cassette also having a second clamp section movable relative to the second guide passage and toward the part of the second tube held in the second guide passage to close the second tube and movable relative to the second guide passage away from the part of the second tube held in the second guide passage to open the second tube, the first clamp section being different from the first and second guide passages, and the second clamp section being different from the first and second guide passages;
 wherein the first and second clamp sections are provided on the same side of the plate section of the cassette; and
 wherein the first clamp section and the second clamp section are in a common plane.

16. The blood bag system according to claim 1, wherein the first clamp section and the second clamp section each are responsive to a first force to be closed and to a second force to be opened.

17. The blood bag system according to claim 2, wherein the first clamp and the second clamp each are responsive to a first force to be closed and to a second force to be opened.

18. The blood bag system according to claim 7, wherein the first clamp section and the second clamp section each are responsive to a first force to be closed and to a second force to be opened.

19. The blood bag system according to claim 8, wherein the first clamp and the second clamp each are responsive to a first force to be closed and to a second force to be opened.

20. The blood bag system according to claim 15, wherein the first clamp section and the second clamp section each are responsive to a first force to be closed and to a second force to be opened.

21. The blood bag system according to claim 2, wherein the first tube is connected to the inlet of the filter with a first tubular body, and the second tube is connected to the outlet of the filter with a second tubular body, the first and second tubular bodies being elongated in a longitudinal direction of the filter.

22. The blood bag system according to claim 2, wherein the first clamp operating section is a cantilever in which one end of the first clamp operating section is fixed in position as the first clamp operating section moves in the plane toward the first clamp and an opposite end of the first clamp operating section is free, and wherein the second clamp operating section is a cantilever in which one end of the second clamp operating section is fixed in position as the second clamp operating section moves in the plane toward the second clamp and an opposite end of the second clamp operating section is free.

23. The blood bag system according to claim 8, wherein the second pressing section of the first clamp operating section is a cantilever in which one end of the first pressing section of the first clamp operating section is fixed in position as the first pressing section of the first clamp operating section moves in the plane and an opposite end of the second pressing section of the first clamp operating section is free, and wherein the second pressing section of the second clamp operating section is a cantilever in which one end of the second pressing section of the second clamp operating section is fixed in position as the second pressing section of the second clamp operating section moves in the plane and an opposite end of the second pressing section of the second clamp operating section is free.

24. The blood bag system according to claim 8, wherein the first pressing section of the first clamp operating section and the second pressing section of the first clamp operating section simultaneously directly contact the first clamp.

* * * * *